US009677093B2

(12) United States Patent
Fernholz et al.

(10) Patent No.: US 9,677,093 B2
(45) Date of Patent: *Jun. 13, 2017

(54) METHOD USING SHORT CHAIN PERACIDS FOR CONTROLLING BIOFUEL FERMENTATION PROCESS INFECTION AND YIELD LOSS

(71) Applicant: Ecolab USA Inc., St. Paul, MN (US)

(72) Inventors: Peter J. Fernholz, Burnsville, MN (US); Jay Kummet, Elko, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,867

(22) Filed: Oct. 6, 2015

(65) Prior Publication Data

US 2016/0024531 A1  Jan. 28, 2016

Related U.S. Application Data

(63) Continuation of application No. 14/457,297, filed on Aug. 12, 2014, now Pat. No. 9,416,375, which is a continuation of application No. 13/923,465, filed on Jun. 21, 2013, now Pat. No. 8,835,140.

(60) Provisional application No. 61/662,620, filed on Jun. 21, 2012.

(51) Int. Cl.
*A01N 37/16* (2006.01)
*C12P 7/10* (2006.01)
*C12P 7/06* (2006.01)

(52) U.S. Cl.
CPC ............... *C12P 7/10* (2013.01); *A01N 37/16* (2013.01); *C12P 7/06* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 1,727,223 A | 9/1929 | VanLoon et al. |
| 5,437,868 A * | 8/1995 | Oakes ............... A01N 37/16 424/405 |
| 5,571,446 A | 11/1996 | Rouillard |
| 5,683,724 A | 11/1997 | Hei et al. |
| 6,042,629 A | 3/2000 | McGarrity |
| 6,204,231 B1 | 3/2001 | Patten et al. |
| 7,498,051 B2 | 3/2009 | Man et al. |
| 7,504,123 B2 | 3/2009 | Man et al. |
| 7,507,429 B2 | 3/2009 | Man et al. |
| 7,569,232 B2 | 8/2009 | Man et al. |
| 8,058,039 B2 | 11/2011 | Dailey et al. |
| 8,828,910 B2 * | 9/2014 | Aksela ............... A01N 37/02 504/160 |
| 8,835,140 B2 * | 9/2014 | Fernholz ............ A01N 37/16 435/161 |
| 9,416,375 B2 * | 8/2016 | Fernholz ............ A01N 37/16 |
| 2004/0044087 A1 | 3/2004 | Maye |
| 2005/0183744 A1 | 8/2005 | Staub et al. |
| 2008/0026215 A1 | 1/2008 | Wan et al. |
| 2008/0194518 A1 | 8/2008 | Mookerjee et al. |
| 2008/0206215 A1 | 8/2008 | Ziegler |
| 2009/0061490 A1 | 3/2009 | Edwards et al. |
| 2009/0087897 A1 | 4/2009 | Sumner et al. |
| 2009/0199875 A1 * | 8/2009 | Fernholz ............ B08B 7/00 134/30 |
| 2009/0200234 A1 * | 8/2009 | Schacht ............. B01D 65/02 210/636 |
| 2009/0233340 A1 | 9/2009 | Dailey et al. |
| 2010/0075006 A1 | 3/2010 | Semenza |
| 2010/0143307 A1 | 6/2010 | Dailey et al. |
| 2010/0261243 A1 | 10/2010 | Kloos |
| 2010/0291649 A1 | 11/2010 | Solomon et al. |
| 2010/0297719 A1 | 11/2010 | de Sa et al. |
| 2011/0054024 A1 | 3/2011 | Maye |
| 2011/0230394 A1 | 9/2011 | Wiatr et al. |
| 2013/0000681 A1 | 1/2013 | Johnson et al. |
| 2013/0017301 A1 | 1/2013 | Hilgren et al. |
| 2013/0203849 A1 | 8/2013 | Ben Yehuda |
| 2013/0224814 A1 | 8/2013 | Semenza et al. |
| 2014/0039050 A1 * | 2/2014 | da Costa ............ A01N 37/16 514/557 |
| 2015/0164071 A1 | 6/2015 | Tiekemeier et al. |

FOREIGN PATENT DOCUMENTS

| | | |
|---|---|---|
| CA | 2300807 A1 | 9/2000 |
| EP | 0231632 A2 | 8/1987 |

(Continued)

OTHER PUBLICATIONS

Agrawal, Renu, et al., "Role of Antimicrobial Agents in Simultaneous Saccharification and Fermentation of Paddy Malt Mash to Ethanol by Mixed Cultures of *Saccharomyces cerevisiae* PH03 and *Zymomonas Mobilis* ZM4", *See art for complete* Jun. 30, 1996.

Brown, J.B., et al., "The Effect of Hydrogen Peroxide on Yeast Growth and Fermentation", Ann. Appl. Biol., p. 428-435 Dec. 31, 1927.

Chang, In Seop, et al., "Use of Sulfite and Hydrogen Peroxide to Control Bacterial Contamination in Ethanol Fermentation", Applied and Environmental Microbiology, vol. 63, No. 1, p. 1-6 Jan. 31, 1997.

Ecolab Inc., "Acid Sanitizer/Disinfectant", Octave, p. 1-2 Dec. 31, 2007.

(Continued)

*Primary Examiner* — Ralph Gitomer
(74) *Attorney, Agent, or Firm* — McKee, Voorhees & Sease, PLC

(57) ABSTRACT

A process for the use of peracid compositions to eliminate and/or control the growth of undesirable bacteria, including contaminating bacteria, in the fermentation production of alcohol is disclosed. Beneficially, the peracid compositions and methods of use of the same do not interfere or inhibit the growth or replication of yeast and have low or no adverse environmental impact.

19 Claims, 10 Drawing Sheets

(56) References Cited

FOREIGN PATENT DOCUMENTS

| JP | 2007124933 A | 5/2007 |
|---|---|---|
| WO | 2007145857 A1 | 12/2007 |
| WO | 2007145858 A1 | 12/2007 |
| WO | 2007149450 A2 | 12/2007 |
| WO | 2009010836 A2 | 1/2009 |
| WO | 2010093765 A1 | 8/2010 |
| WO | 2012027469 A2 | 3/2012 |
| WO | 2012027469 A3 | 3/2012 |
| WO | 2012037294 A2 | 3/2012 |
| WO | 2012113042 A1 | 8/2012 |
| WO | 2013156813 A1 | 10/2013 |

OTHER PUBLICATIONS

Hynes, SH, et al., "Use of Virginiamycin to Control the Growth of Lactic Acid Bacteria During Alcohol Fermentation", Journal of Industrial Microbiology & Biotechnology, 18, p. 284-291 Dec. 31, 1997.

Narendranath, N. V., et al., "Effects of Lactobacilli on Yeast-Catalyzed Ethanol Fermentations", Applied and Environmental Microbiology, vol. 63, No. 11, p. 4158-5163 Nov. 30, 1997.

Narendranath, N. V., et al., "Urea Hydrogen Peroxide Reduces the Numbers of Lactobacilli, Nourishes Yeast, and Leaves no Residues in the Ethanol Fermentation", Applied and Environmental Microbiology, vol. 66, No. 10, p. 4187-4192 Oct. 31, 2000.

Oliva-Neto, Pedro-de, et al., "Effect of 3,4,4'-Trichlorocarbanilide on Growth of Lactic Acid Bacteria Contaminants in Alcoholic Fermentation", Bioresource Technology 63, p. 17-21 Dec. 31, 1998.

Semenza, Reed, "Controlling Bacteria During Corn Mash Fermentation", http://www.ethanolproducer.com/articles/7857/controlling-bacteria-during-corn-mash-fermentation, retrieved from the Internet on Jun. 14, 2012.

Storgards, E., "Process Hygiene Control in Beer Production and Dispensing", Academic Dissertation from Technical Research Centre of Finland, Espoo, p. 1-106 Apr. 30, 2000.

Hilgren, J., et al., "Inactivation of Bacillus anthracis Spores by Liquid Biocides in the Presence of Food Residue", Appl. Environ. Microbiol., Oct. 2007, vol. 73, No. 20, 6370-6377, retrieved from the Internet on Jan. 22, 2015.

United States Patent and Trademark Office, "Non-Final Office Action" issued in connectionw ith U.S. Appl. No. 13/817,955, 25 pages, mailed on May 26, 2015.

Barth, D., et al., "DesinFix TM 135 in fermentation process for bioethanol production", Brazilian Journal of Microbiology 45, 1, 323-325 Sep. 9, 2013.

Kalogiannis, K., "Lignocellulosic Biomass Fractionation as a Pretreatment Step for Production of Fuels and Green Chemicals", Waste and Biomass Valorization (2015) Ahead of Print CODEN: WBVAAG; ISSN: 1877-2641 May 30, 2015.

ECOLAB Octave FS spec sheet, 2 pages, issued Dec. 31, 2007.

Baldry, "The bactericidal, fungicidal and sporididal Properties of hydrogen peroxide and peracetic acid", Journal of Applied Bacteriology, published on Nov. 29, 1982.

* cited by examiner

METHOD USING SHORT CHAIN PERACIDS FOR CONTROLLING BIOFUEL FERMENTATION PROCESS INFECTION AND YIELD LOSS

CROSS-REFERENCE TO RELATED APPLICATIONS

This application is a continuation application of U.S. Ser. No. 14/457,297 filed Aug. 12, 2014, now U.S. Pat. No. 9,416,375 issued Aug. 16, 2016, which is a continuation application of U.S. Ser. No. 13/923,465 filed Jun. 21, 2013, now U.S. Pat. No. 8,835,140 issued Sep. 16, 2014, which claims priority to provisional application of U.S. Ser. No. 61/662,620 filed Jun. 21, 2012, which are hereby incorporated by reference in their entireties.

BACKGROUND OF THE INVENTION

The biofuel industry employs yeast to covert sugars into ethanol. A problem in the industry is that fermentation process equipment and/or the mash can become contaminated with bacteria that reduce production yields. As a result, the efficiency of such ethanol fermentation is significantly limited by other micro-organisms contaminating the process, including for example lactic acid and acetic acid bacteria (e.g. yield loss bacterium). Such contaminating bacteria complete for sugar supply with the yeast, resulting in a decrease in ethanol production. In addition, the contaminating bacteria can decrease the pH conditions which further inhibit the growth of ethanol-producing yeast. *Lactobacillus* and *Acetobacter* are well-known yield loss bacterium in the ethanol fermentation industry. As a result, there is a need for preventing ethanol fermentation yield loss from bacterial infection introduced in ethanol fermentation procedures.

Antibiotics are commonly used as a means for controlling unwanted yield loss bacterium in fermentation plants. However, the byproducts of corn ethanol fermentation, including distiller's wet grain solids (i.e. wetcake byproduct) are often used for feed supplies. For example, distiller's grain and dried yeast are frequently used for beef and dairy cattle feed. The conventional use of antibiotics, such as virginiamycin, in the ethanol fermentation methods for controlling yield loss undesirably results in the incidental (i.e. sub-therapeutic) dosing of antibiotics to such animals. Data confirms the survival of antibiotics through the distillation process at low levels into the byproducts. There is significant public opposition to such incidental antibiotic dosing into animal feed supplies, as well as suggested regulatory (Food and Drug Administration) consideration for the banning of the use of antibiotics in the ethanol industry. In addition, the use of antibiotics is costly. Therefore, there is a clear desire to eliminate the use of such antibiotics from the corn ethanol fermentation process.

Antibiotic alternatives have included oxidizing biocides, such as stabilized chlorine dioxide, which may be pumped into a fermenter prior to the fermentable substrate being loaded. During the course of fermentation, the organic acids produced by contaminating bacteria are thought to activate the chlorine dioxide in the vicinity of the bacterial cells. Chlorine dioxide has also been used for disinfecting process pipes and heat exchangers. Other antibiotic alternatives that have been employed in limited fashion include inorganic oxidizers, such as hydrogen peroxide or urea hydrogen peroxide.

A chemical alternative to antibiotics for use in the biofuel industry includes peracids. Peracids are known for use as sanitizers, disinfectants, deodorizers, and bleaching agents, among other uses. Peracids are particularly well suited for use in both clean-in-place systems (CIP) and clean-out-of-place systems (COP), as well as industrial uses including antimicrobial control for washing or processing meat surfaces, vegetable fume applications, food and beverage applications and the like. See U.S. Pat. Nos. 7,498,051, 7,504,123, 7,507,429, and 7,569,232, which are herein incorporated by reference in their entirety. However, such CIP and/or COP methods have not reportedly been used in the fermentation industry. Accordingly, it is an objective of the claimed invention to develop methods, compositions and systems for improved cleaning and sanitation procedures using peracids for use in ethanol fermentation processes.

A further object of the invention is to develop methods, compositions and systems for improved ethanol yield in ethanol fermentation processes through the elimination of unwanted bacterial infiltration.

A further object of the invention is an improved yield loss control for ethanol fermentation to replace the convention use of antibiotics in the field.

BRIEF SUMMARY OF THE INVENTION

An advantage of the invention is a non-antibiotic solution to ethanol fermentation yield management through the use of peracid compositions, namely peroxyoctanoic acids. It is an advantage of the present invention that the use of peracid compositions improves ethanol yield without creating any residual animal feed concerns. As a result, the peracid compositions and methods of employing the same in fermentation processes overcome a significant need in the art for improved sanitization methods and yield loss management. These and other unexpected benefits achieved by the present invention are disclosed herein.

In an aspect of the invention, a method for reducing and/or eliminating microbial populations in a fermentation system comprising: applying a peracid composition to sanitize a fermentation system, wherein the peracid composition comprises a medium chain peracid and wherein the fermentation system comprises one or more fermentation vessels, pipes and/or components; providing or obtaining a mash sources in said fermentation system; and reducing and/or eliminating a microbial population of yield loss organisms in said fermentation system.

In a further aspect of the invention, method for reducing yield loss in ethanol fermentation processes comprising: applying a peracid composition to sanitize a fermentation system, wherein the peracid composition comprises a medium chain peracid; fermenting a mash in the presence of at least a residual portion of said peracid composition and yeast in a vessel of said fermentation system to produce ethanol and a solids content; reducing a microbial population of lactic acid bacteria and/or acetic acid bacteria; and distilling the fermented mash to separate at least a portion of the ethanol from said solids content. In a further aspect, the antimicrobial efficacy of said peracid composition does not interfere with yeast fermentation.

In a still further aspect, the invention discloses a method for replacing antibiotics in fermentation processes comprising: replacing an antibiotic used in a fermentation process to reduce and/or eliminate *Lactobacillus* and/or *Acetobacter* species with a peracid composition for application to a fermentation system; and introducing the peracid composition to a mash source, wherein the peracid composition comprises from about 0.0005 wt-% to about 5 wt-% peroxyoctanoic acid, from about 1 wt-% to about 10 wt-% octanoic acid, from about 5 wt-% to about 97 wt-% water, from about 0 wt-% to about 20 wt-% anionic surfactant, from about 0 wt-% to about 10 wt-% oxidizing agent; about 0 wt-% to about 35 wt-% inorganic acid, and from about 0 wt-% to about 5 wt-% sequestrant, and wherein the peracid composition does not interfere with yeast fermentation in a fermentation process.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
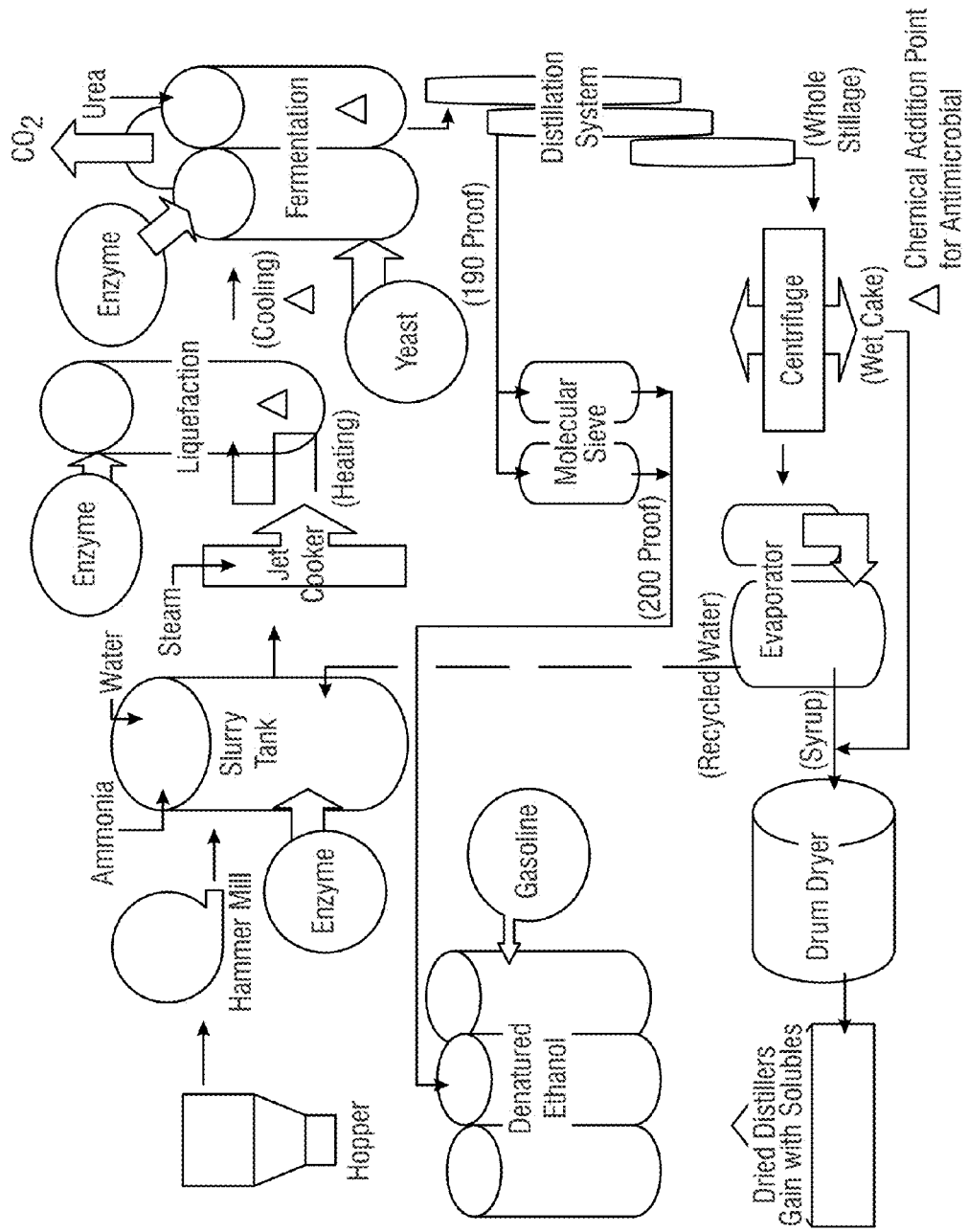
FIG. 1 shows a process flow diagram of one or more methods of ethanol production including optimal locations for the addition of the peroxyoctanoic acid (or other peracid composition) treatment according to the invention employing a peracid composition.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to non-antibiotic sanitizing and ethanol yield improvement methods for use in the biofuels industry. The peracid compositions and methods of employing the same have many advantages over conventional antibiotic methods of controlling yield loss in ethanol fermentation. For example, the use of peracid compositions, namely peroxyoctanoic acids, providing sanitization benefits for the fermentation system, without causing false positive results in system contamination. In addition, the use of peracid compositions improves ethanol yield without creating any residual animal feed concerns.

The embodiments of this invention are not limited to particular methods and/or peracid compositions for controlling fermentation processes to prevent infection and/or reduce yield losses, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "antibiotic," as used herein, refers to a substance well known to skilled artisans that controls the growth of bacteria, fungi, or similar microorganisms, wherein the substance can be a natural substance produced by bacteria or fungi, or a chemically/biochemically synthesized substance (which may be an analog of a natural substance), or a chemically modified form of a natural substance.

The term "cellulosic material," as used herein, refers to material containing cellulose. Cellulose is generally found, for example, in the stems, leaves, hulls, husks, and cobs of plants or leaves, branches, and wood of trees. The cellulosic material can be, but is not limited to, herbaceous material, agricultural residues, forestry residues, municipal solid wastes, waste paper, and pulp and paper mill residues. It is understood herein that the cellulose may be in the form of lignocellulose, a plant cell wall material containing lignin, cellulose, and hemicellulose in a mixed matrix.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "Distillers Dried Grains" (DDG), as used herein refers generally to coproducts of ethanol production by fermentation which can comprise dried residual grain solids, which can be animal feed grade. "Distillers Dried Grains with Solubles" (DDGS) refers to coproducts of ethanol production by fermentation which can comprise dried residual grain solids with solubles content, such as process syrup or other solubles, and which can be animal feed grade. "Wet Distillers Grains" (WDG) refers to coproducts of ethanol production by fermentation which can comprise residual grain solids prior to drying, which can contain at least a portion of process syrup, and which can be animal feed grade.

As used herein, the term "fermentable sugar" refers to simple sugars such as monosaccharides and disaccharides (e.g., glucose (dextrose), fructose, galactose, sucrose, maltose) that can be used by yeast or other microorganisms in conversions to ethanol or other end products.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid (POAA) and peroxyoctanoic acid (POAA).

As used herein, the terms "peracid" or "peroxy acid" refer to an acid having the hydrogen of the hydroxyl group replaced by a hydroxy group. Oxidizing peracids are referred to herein as peroxycarboxylic acids.

As used herein the term "peracid forming composition" refers to a composition that produces a peracid when the components of the composition are combined. For example, in some embodiments, a peracid forming composition suitable for use in the present invention includes an organic acid and an oxidizing agent.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60 C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60 C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Compositions

According to an embodiment of the invention a peracid composition is employed for fermentation procedures, namely in the biofuels industry. In an aspect, the peracid compositions according to the invention may include a peracid (e.g., a peroxycarboxylic acid or a sulfoperoxycarboxylic acid) or mixture thereof.

In a further aspect, the peracid composition can also include an organic acid and an oxidizing agent. In a still further aspect, the peracid composition can be a peracid forming composition. In various aspects the peracid composition can be formed by an organic acid and an oxidizing agent. In other aspects, peracid forming compositions may be employed to generate a peracid composition in situ. Additional description of exemplary in situ methods for peracid forming compositions is provided in U.S. application Ser. Nos. 13/331,304 and 13/331,486 (Ecolab Cases 2757USU1 and 2757USU2), which are herein incorporated by reference in its entirety.

The concentration of peracids employed in a peracid composition according to the invention is suitable to replace the antibiotic dependent methods of fermentation. In an aspect, the concentration of peracids is sufficient to sanitize a fermentation system (or portion thereof) or a mash source. In a further aspect, the concentration of peracids is sufficient to control the problematic yield loss bacteria without reducing the yeast required for the ethanol fermentation.

In an aspect, peracid compositions are suitable for use according to the methods of the invention at concentrations employed for surface disinfection. For example, concentrations of peracid compositions suitable for use in non-food contact surface disinfection may be employed. In a further aspect, peracid compositions can be employed at a concentration up to about 20,000 ppm. In another aspect, peracid compositions can be employed at a concentration up to about 10,000 ppm. In a still further aspect, a medium chain peracid composition can be employed at concentrations from about 2,500 ppm to about 10,000 ppm. Without being according to the invention, all ranges recited are inclusive of the numbers defining the range and include each integer within the defined range.

In other aspects according to the invention, more dilute concentrations of the peracid compositions can be employed. For example, in methods using a CIP surface disinfection a surface disinfecting amount of the peracid composition is employed. Thereafter a residual amount of the peracid composition is used as a preservative for a mash source. In an aspect, the peracid compositions are suitable for use according to the methods of the invention at concentrations up to about 2,000. In other aspects, the residual amounts of the peracid compositions are used at concentrations from about 1 ppm to about 2,000 ppm, and from about 1 ppm to about 500 ppm. Without being according to the invention, all ranges recited are inclusive of the numbers defining the range and include each integer within the defined range.

The peracid compositions according to the invention do not carry through the fermentation and/or distillation process in amounts or concentrations that cause animal feeding concerns and/or regulatory concerns. In addition, the use of peracid compositions do not contribute to public health concerns associated with antibiotic-resistant strains of bacteria found in the ethanol fermentation process.

Peroxycarboxylic Acids

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide.

Peroxycarboxylic acids may include short chain and/or medium chain peroxycarboxylic acids. As used herein, the phrase "medium chain peroxycarboxylic acid" refers to the peroxycarboxylic acid form of a medium chain carboxylic acid. As used herein, the phrase "medium chain carboxylic acid" refers to a carboxylic acid that: 1) has reduced or is lacking odor compared to the bad, pungent, or acrid odor associated with an equal concentration of small chain carboxylic acid, and 2) has a critical micellar concentration greater than 1 mM in aqueous buffers at neutral pH. Medium chain carboxylic acids exclude carboxylic acids that are infinitely soluble in or miscible with water at 20 C. Medium chain carboxylic acids include carboxylic acids with boiling points (at 760 mm Hg pressure) of 180 to 300° C. In an embodiment, medium chain carboxylic acids include carboxylic acids with boiling points (at 760 mm Hg pressure) of 200 to 300° C. In an embodiment, 20 medium chain carboxylic acids include those with solubility in water of less than 1 g/L at 25° C. Examples of medium chain carboxylic acids include pentanoic acid, hexanoic acid, heptanoic acid, octanoic acid, nonanoic acid, decanoic acid, undecanoic acid, and dodecanoic acid.

As used herein, the phrase "short chain peroxycarboxylic acid" refers to the peroxycarboxylic acid form of a short chain carboxylic acid. As used herein, the phrase "short chain carboxylic acid" refers to a carboxylic acid that: 1) has characteristic bad, pungent, or acrid odor, and 2) is infinitely soluble in or miscible with water at 20° C. Examples of short chain carboxylic acids include formic acid, acetic acid, propionic acid, and butyric acid. In a preferred aspect of the invention, short chain carboxylic acids are not employed. In particular, acetic acids are not employed according to a preferred embodiment of the invention. In some embodiments, the compositions and methods of the present invention do not include peroxyacetic acid or acetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof.

In some embodiments, the compositions of the invention utilize a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the C1 to C4 peroxycarboxylic acid is peroxyacetic acid and the C5 to C11 acid is peroxyoctanoic acid.

In some embodiments, the compositions and methods of the present invention include peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of microbes. Peroxyoctanoic acid can be prepared through any number of methods known to those of skill in the art. A solution of peroxyoctanoic acid can be obtained by combining octanoic acid and hydrogen peroxide. In an aspect of the invention a commercially-available peroxyoctanoic acid containing product is available under the commercial name Octave (Ecolab, Inc.). Additional description of particularly suitable peroxyoctanoic acids is disclosed in U.S. Pat. Nos. 7,498,051, 7,504,123, 7,507,429 and 7,569,232, which are herein incorporated by reference.

In a preferred aspect of the invention, the peracid does not include a peracetic acid and/or acetic acid (organic acid source). There is an additional unexpected benefit of employing a peroxyoctanoic acid according to an embodiment of the invention. In particular, use of the peroxyoctanoic acid avoids introduction of acetic acid, which is common to many commercial peracid sanitizing compositions. Acetic acid has been demonstrated to detrimentally result in false positive tests on quality control applications; the organic acid appears on plant quality control tests (e.g. Gas Chromatography) as a false indicator of infection with acid-forming bacteria. As a result the peracid compositions and methods of employing the same according to the invention that employs a peroxyoctanoic acid composition due to result in false positive indicators of acid-forming bacteria infecting a fermentation system.

In some embodiments, the compositions of the present invention include about −0.0005 wt-% to about 20 wt-%, about 0.3 wt-% to about 10 wt-%, about 0.5 wt-% to about 5.0 wt-%, about 1 wt-% to about 3 wt-%, or about 1 wt-% to about 2 wt-% of one or more peroxycarboxylic acids. It is to be understood that all values and ranges between these values and ranges are encompassed by the present invention.

Sulfoperoxycarboxylic Acids

Sulfoperoxycarboxylic (or sulfopercarboxylic) acids generally have the formula

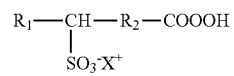

wherein $R_1$ is hydrogen, or a substituted or unsubstituted alkyl group; $R_2$ is a substituted or unsubstituted alkyl group; X is hydrogen, a cationic group, or an ester forming moiety; or salts or esters thereof. In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof. In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group.

In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkyl group.

In some embodiments, $R_1$ is a substituted C8-C10 alkyl group is substituted with at least 1, or at least 2 hydroxyl groups. In still yet other embodiments, $R_1$ is a substituted C1-C9 alkyl group. In some embodiments, $R_1$ is a substituted C1-C9 substituted alkyl group is substituted with at least 1 $SO_3H$ group.

In other embodiments, $R_1$ is a C9-C10 substituted alkyl group. In some embodiments, $R_1$ is a substituted C9-C10 alkyl group wherein at least two of the carbons on the carbon backbone form a heterocyclic group. In some embodiments, the heterocyclic group is an epoxide group.

In some embodiments, $R_2$ is a substituted C1 to C10 alkyl group. In some embodiments, $R_2$ is a substituted C8-C10 alkyl. In some embodiments, $R_2$ is an unsubstituted C6-C9 alkyl. In other embodiments, $R_2$ is a C8 to C10 alkyl group substituted with at least one hydroxyl group. In some embodiments, $R_2$ is a C10 alkyl group substituted with at least two hydroxyl groups. In other embodiments, $R_2$ is a C8 alkyl group substituted with at least one $SO_3H$ group. In some embodiments, $R_2$ is a substituted C9 group, wherein at least two of the carbons on the carbon backbone form a heterocyclic group. In some embodiments, the heterocyclic group is an epoxide group. In some embodiments, $R_1$ is a C8-C9 substituted or unsubstituted alkyl, and $R_2$ is a C7-C8 substituted or unsubstituted alkyl.

Additional description of particularly suitable sulfoperoxycarboxylic acids is disclosed in U.S. Pat. No. 8,344,026 and U.S. patent application Ser. Nos. 12/568,493 and 13/290,355 which are herein incorporated by reference in their entirety.

Without wishing to be bound by any particular theory, it is thought that mid-chain sulfonated peracids, e.g., mid-chain sulfonated peracids with a C10-C18 carbon backbone have a substantially greater solubility compared to terminally sulfonated peracids of a similar chain length, even at an acidic pH. For example, at a pH of 4, the terminally sulfonated peracid, 11-sulfoundecane peroxoic acid has a relatively low solubility of about 1.3%. At the same pH, the mid chain sulfonated peracid, persulfonated oleic acid has a solubility of greater than about 50%. This is unexpected as an increase in peracid chain length is thought to lead to a decrease in solubility. The issue of low solubility when using long chain peracids has been addressed by increasing the pH to above 7. However, at increased pH antimicrobial efficacy is substantially reduced. Further, bleaching efficacy decreases proportionally with every pH unit increase over about 7. Thus, solubility at an acidic pH (lower than about 7) is beneficial to the mid-chain sulfonated peracids of the present invention.

In some embodiments, the compositions of the invention utilize a combination of several different sulfoperoxycarboxylic acids. For example, in some embodiments, the composition includes one or more C1 to C4 sulfoperoxycarboxylic acids and one or more C5 to C11 sulfoperoxycarboxylic acids.

The sulfoperoxyacids disclosed according to the invention can be formed using a variety of reaction mechanisms. For example, in some embodiments, the peracids are formed by the direct acid catalyzed equilibrium action of hydrogen peroxide with the starting materials.

In some embodiments, the compositions of the present invention include about −0.0005 wt-% to about 20 wt-%, about 0.3 wt-% to about 10 wt-%, about 0.5 wt-% to about 5.0 wt-%, about 1 wt-% to about 3 wt-%, or about 1 wt-% to about 2 wt-% of one or more sulfoperoxycarboxylic acids. It is to be understood that all values and ranges between these values and ranges are encompassed by the present invention.

Organic Acids

The peracid compositions may also include at least one organic acid. Any organic acid capable of forming a peracid can be used in the compositions and methods of the present invention. Suitable organic acids for use with the present invention include, but are not limited to, carboxylic acids.

In some embodiments, the compositions of the present invention include at least one carboxylic acid. In some embodiments, the compositions of the present invention include at least two, at least three, or at least four or more carboxylic acids.

In some embodiments, the carboxylic acid for use with the compositions of the present invention is a C1 to C22 carboxylic acid. In some embodiments, the carboxylic acid for use with the compositions of the present invention is a C5 to C11 carboxylic acid. In some embodiments, the carboxylic acid for use with the compositions of the present invention is a C1 to C4 carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

In some embodiments, the compositions of the present invention include about 10 wt-% to about 95 wt-%, about 25 wt-% to about 80 wt-%, or about 50 wt-% to about 75 wt-% of a carboxylic acid. In some embodiments, the compositions of the present invention include acetic acid. In other embodiments, the compositions of the present invention include octanoic acid. In other embodiments, the compositions of the present invention include a combination of octanoic acid and acetic acid.

Oxidizing Agent

The peracid compositions may also include an oxidizing agent. The oxidizing agent can be effective to convert an acid into a peracid. The oxidizing agent may include a peroxide source. Oxidizing agents suitable for use with the compositions include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]\cdot 6H_2O$ (also called sodium perborate tetrahydrate); sodium peroxyborate tetrahydrate of the formula $Na_2B_2(O_2)_2[(OH)_4]\cdot 4H_2O$ (also called sodium perborate trihydrate); sodium peroxyborate of the formula $Na_2[B_2(O_2)_2(OH)_4]$ (also called sodium perborate monohydrate); group 14 (WA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some embodiments, the oxidizing agent includes hydrogen peroxide, or a source or donor of hydrogen peroxide. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water.

The compositions may contain an effective amount of an oxidizing agent. In some embodiments, the compositions include about 0.001 wt-% to about 60 wt-% of the oxidizing agent, or about 1 wt-% to about 25 wt-% of the oxidizing agent. In some embodiments, the compositions include about 30 wt-% to about 50 wt-% of the oxidizing agent. It is to be understood that all ranges and values between these ranges and values are encompassed by the present invention.

Solubilizer

The present peracid compositions can include a solubilizer. The present invention relates to solubilizers for various peroxycarboxylic acids, including preferably peroxyoctanoic acid. In an embodiment, the solubilizer can increase or maintain the solubility in the composition. The present compositions and methods can include any of a variety of suitable solubilizers. For example, the solubilizer can include a solvent, a surfactant, or a mixture thereof as disclosed herein. Further description of solubilizers particularly well suited for use with peroxyoctanoic acid compositions is found in U.S. Pat. Nos. 7,498,051 and 7,569,232, which are herein incorporated by reference in their entirety.

Solvent

In some embodiments, the peracid compositions of the present invention are liquids. Therefore, in some embodiments, the compositions of the invention further include a solvent or solubilizer. In some embodiments, the solvent is water. The water may be provided by the use of aqueous reagents, viz. oxidizing agent. In other embodiments, an additional amount of water is added to the peracid compositions.

In some embodiments, the liquid composition according to the present invention is a composition including more than 10 wt-% water but less than 90 wt-%. The amount of water included in the liquid composition can be for example, less than about 80 wt-%, less than about 70 wt-%, and less than about 60 wt-% by weight of the liquid composition. In some embodiments, the composition can contain water between about 5 wt-% and about 50 wt-%, about 10 wt-% and about 40 wt-%, or about 30 wt-%. It is to be understood that all values and ranges between these values and ranges are encompassed by the methods of the present invention.

Alternatively, the compositions may be free of or substantially free of any added water. A non-aqueous solvent may also be used in the compositions. For example, in some embodiments, an alcohol is included as a solvent in the compositions. In some embodiments, a liquid composition of the invention is substantially non-aqueous (or anhydrous) in character. The term "substantially non-aqueous" as used herein means that while very small amounts of water may be incorporated into such preferred compositions, the amount of water in the non-aqueous liquid detergent compositions of the invention are less than about 30 wt-% of the composition. In some embodiments, the water content of the non-aqueous compositions will include less than about 10 wt-% by weight.

The compositions may include an effective amount of solvent. In some embodiments, the compositions may include about 10 wt-% to about 99 wt-% of a solvent, or about 20 wt-% to about 80 wt-% of a solvent. In other embodiments, the compositions may include more than about 30 wt-%, more than about 50 wt-%, more than about 60 wt-% or more than 70% of a solvent. It is to be understood that all values and ranges between these values and ranges are encompassed by the present invention.

Additional Functional Ingredients

The peracid compositions may also include additional functional ingredients. Additional functional ingredients suitable for use in the present compositions include, but are not limited to, stabilizing agents, surfactants, acidulants, hydrotropes, dispersants, antimicrobial agents, optical tracers, solidification agent, aesthetic enhancing agent (i.e., colorant (e.g., pigment), odorant, or perfume), wetting agents, defoaming agents, thickening or gelling agents, among any number of constituents which can be added to the composition. Such adjuvants can be preformulated with the peracid compositions or added to the compositions after formation, but prior to use. The compositions can also contain any number of other constituents as necessitated by the application, which are known and which can facilitate the activity of the present compositions.

Stabilizing Agents

Stabilizing agents are commonly added to equilibrium peracid compositions to stabilize the peracid and hydrogen peroxide and prevent the decomposition of these constituents. Examples of stabilizing agents may include for example, surfactants, couplers, hydrotropes, acid catalysts and the like that are conventionally used in equilibrium peracid compositions to stabilize and improve shelf life of the composition. Further examples of stabilizing agents include, for example, chelating agents or sequestrants. Such sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid). Dipicolinic acid, 1-hydroxy ethylidene-1,1-diphosphonic acid $(CH_3C(PO_3H_2)_2OH)$ (HEDP) are further example of stabilizing agents.

Additional examples of stabilizing agents commonly used in equilibrium chemistry to stabilize the peracid and hydrogen peroxide and/or prevent the premature oxidation of the composition include phosphonic acid or phosphonate salt. Phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are well known as used stabilizing agents.

Surfactants

In some embodiments, the peracid compositions of the present invention may include a surfactant. Surfactants may be included as a solubilizer for the peracid compositions (e.g. microemulsion forming surfactant). Surfactants suitable for use with the compositions of the present invention include, but are not limited to, anionic surfactants, nonionic surfactants, cationic surfactants, amphoteric surfactants, zwitterionic surfactants, mixtures thereof, or the like.

The solubilizer can include a microemulsion forming surfactant. Suitable microemulsion forming surfactants include anionic surfactants, cationic surfactants, amphoteric surfactants, zwitterionic surfactants, mixtures thereof, or the like. Suitable microemulsion forming surfactants include anionic surfactants, such as sulfate surfactant, sulfonate surfactant, phosphate surfactant (phosphate ester surfactant), and carboxylate surfactant, mixtures thereof, or the like.

Preferred Compositions

In an aspect of the invention preferred peracid compositions for use according to the invention comprise, consist of and/or consist essentially of: a medium chain peroxycarboxylic acid. The medium chain peroxycarboxylic acid may include peroxyoctanoic acid; octanoic acid; and water. The medium chain peroxycarboxylic acid may also include a stabilizer, such as polyalkylene oxide, mono alkyl ether of polyalkylene oxide, dialkyl ether of polyalkylene oxide, nonionic surfactant, anionic surfactant, or mixture thereof. In a preferred aspect, the compositions include at least about 2 parts by 35 weight of peroxyoctanoic acid for each 7 parts by weight of octanoic acid.

In additional aspects, the preferred peracid compositions may comprise, consist of and/or consist essentially of: a medium chain peroxycarboxylic acid composition. The medium chain peroxycarboxylic acid composition may include a peroxycarboxylic acid that includes about 0.0005 wt-% to about 5 wt-% peroxyoctanoic acid; about 0.001 wt-% to about 10 wt-% octanoic acid; and about 5 wt-% to about 99.99 wt-% water.

In additional aspects, the preferred peracid compositions may comprise, consist of and/or consist essentially of: a medium chain peroxycarboxylic acid composition. The medium chain peroxycarboxylic acid composition may include about 0.5 wt-% to about 5 wt-% peroxyoctanoic acid; about 1 wt-% to about 10 wt-% octanoic acid; about 5 wt-% to about 97 wt-% water; about 1 wt-% to about 20 wt-% anionic surfactant; about 5 wt-% to about 10 wt-% hydrogen peroxide and/or a persulfate; about 15 wt-% to about 35 wt-% inorganic acid (e.g. sulfuric acid or methanesulfonic acid); and about 1 wt-% to about 5 wt-% sequestrant; the composition comprising a microemulsion.

In additional aspects, the preferred peracid compositions may comprise, consist of and/or consist essentially of: a medium chain peroxycarboxylic acid composition. The medium chain peroxycarboxylic acid composition may include about 0.5 wt-% to about 5 wt-% peroxyoctanoic acid; about 1 wt-% to about 10 wt-% octanoic acid; about 5 wt-% to about 97 wt-% water; about 1 wt-% to about 20 wt-% anionic surfactant; about 5 wt-% to about 10 wt-% oxidizing agent; about 15 wt-% to about 35 wt-% inorganic acid; and about 1 wt-% to about 5 wt-% sequestrant; the composition comprising a microemulsion.

In additional aspects, the preferred peracid compositions may comprise, consist of and/or consist essentially of: a medium chain peroxycarboxylic acid composition. The medium chain peroxycarboxylic acid composition may include about 0.0005 wt-% to about 5 wt-% peroxyoctanoic acid; about 0.001 wt-% to about 10 wt-% octanoic acid; about 40 wt-% to about 99.99 wt-% water; about 0.001 wt-% to about 60 wt-% polyalkylene oxide, monoalkyl ether of polyalkylene oxide, dialkyl ether of polyalkylene oxide, anionic surfactant, nonionic surfactant, or mixture thereof, or mixture thereof; about 0.002 wt-% to about 10 wt-% oxidizing agent; about 0.001 wt-% to about 30 wt-% inorganic acid; and about 0.001 wt-% to about 5 wt-% sequestrant.

The preferred compositions for use in the methods of the invention provide the various benefits not previously achieved by others employing peracid compositions. See U.S. patent application Ser. No. 13/048,972 (Buckman Laboratories International, Inc.), which is herein incorporated by reference. The prior art employing certain nonoxidizing biocides, including peracetic acid, has not employed the superior efficacy of the medium chain peroxycarboxylic acids, namely peroxyoctanoic acid compositions. In addition, the methods of application and use disclosed in the invention represent additional improvements over the art.

Systems for Ethanol Fermentation

Systems and methods for ethanol fermentation are well known in the art. In general, the processes for converting a complex carbohydrate or starch to fermentable sugar includes the following steps: a grain or cereal containing granular starch (e.g. cellulosic material such as corn) is obtained; a milling step is employed (e.g. wet milling or dry milling); mixing milled starch-containing material with an aqueous solution to produce a slurry; liquefaction processing (if required); addition of a suitable enzyme (if required); saccharification; purification (if required); and finally metabolization/fermentation by a fermenting microorganism (e.g. yeast) to create ethanol. As one of skill in the art appreciates, the saccharification and fermentation steps may be carried out sequentially or simultaneously. The final step is the distillation of the fermented mass to separate ethanol product from the remaining byproduct (e.g. stillage), which can be processed to form distillers dried grains.

The methods of the invention that are disclosed herein are suitable for use in various applications of fermentation methods. This includes varying the sources of cellulosic materials or feedstock materials. For example, without being limited to a particular theory of the invention, the present invention using peracid compositions for yield loss bacteria control can be used without limitation with respect to the feedstock source for the methods of ethanol fermentation.

Examples of suitable feedstock sources, include for example, agricultural crops, such as grains (e.g., corn, wheat, grain sorghum, barley, rice, sugar cane, and the like); agricultural waste associated with crops; lignocellulosic biomasses (e.g. wood chips, corn stover, corn cobs, straw, grain hulls, recycled papers and the like); fruits and/or fruit juices; refined sugars; combinations of the same; and other feedstock sources appreciated by those skilled in the art.

Further description of the methods and system set-up customarily employed in ethanol fermentation are shown in FIG. 1, which is a non-limiting embodiment of systems according to the invention. As demonstrated in FIG. 1, the peracid compositions, such as a peroxyoctanoic acid composition, may be added into an ethanol process within a CIP process, directed additive, or both. As is described in more detail herein, the use of peracid compositions according to the invention are particularly suitable for cleaning the apparatus/systems employed for the ethanol process (e g tanks, cookers, fermentation vessels and the like). In addition, according to various embodiments of the invention the peracid compositions may be employed upstream from the fermentation vessels of the system.

Methods

The methods employing the peracid compositions according to the invention are suitable for various applications in fermentation processes and systems, namely in the biofuels industry. Fermentation processes may include, for example, ethanol plants which may use a variety of substrates such as corn and cane sugar. For example, it is contemplated that the peracid compositions are suitable for system sanitation (e.g. tank/vessel sanitation) as well as a process aid to improve fermentation yield without the introduction of antibiotics.

According to an embodiment the invention, methods for reducing and/or eliminating microbial populations in a fermentation system are provided. In some aspects, the methods of treating microbial populations are effective for killing one or more of the pathogenic bacteria associated with ethanol fermentation methods. Such bacteria include a wide variety of microorganisms, such as aerobic and anaerobic bacteria, including Gram positive and Gram negative bacteria, yeast, molds, bacterial spores, viruses, etc. In particular, the methods of the invention are particularly suitable for use against lactic acid bacteria. "Lactic acid bacteria," as used herein, refers to a class of bacteria including, for example, *Lactobacillus, Pediococcus, Leuconostoc* and *Weissella* species. Acetic acid bacteria, e.g., *Acetobacter* species, can also cause problems by producing acetic acid or other organic acids which foul the process and reduce the yields of ethanol.

In a preferred aspect of the invention, the peracid compositions and methods of employing the same for reducing and/or eliminating microbial populations in a fermentation system do not interference with yeast performance.

According to an embodiment the invention, methods for reducing yield loss in ethanol fermentation are provided. In an aspect of the invention the use of peracid compositions according to the invention are employed to reduce and/or eliminate bacterial infiltration or infection of a fermentation system. The peracid compositions are employed for use as a surface sanitizer.

According to a further embodiment, methods for replacing antibiotics in ethanol fermentation processes are provided. In an aspect, a non-antibiotic dependent method for controlling yield loss in a fermentation process is provided. In an embodiment, the use of a peracid composition in the ethanol fermentation process replaces the conventional use of antibiotics. Still further, the use of the peracid compositions according to these methods not only provide a high degree of antimicrobial efficacy, the resultant fermentation byproducts are further safely ingested by animals as a feed supply while imposing no unacceptable environmental incompatibility.

The various methods of the invention include may comprise, consist of and/or consist essentially of one or more of the following steps: sanitizing a fermentation vessel; sanitizing one or more fermentation vessels, pipes and/or components (including downstream equipment employed for fermentation); sanitizing a fermentation source (e.g. mash) or other component with a peracid composition; and the like.

In an aspect of the invention, a peracid composition is introduced into a vessel or system/apparatus employed for ethanol fermentation to sanitize the surface against unwanted bacterial agents, namely yield loss agents. The introduction of the peracid composition is employed for hard surface cleaning and sanitizing, which may include clean-in-place systems (CIP) and/or clean-out-of-place systems (COP). For ethanol fermentation processes, COP systems may include for example readily accessible systems including wash tanks/vessels, fermentation vessels, other tanks/vessels, removable system parts, and the like. For ethanol fermentation processes, CIP systems may include the internal components of tanks, lines, pumps and other process equipment used for processing typically liquid product streams. Beneficially, the treatment of the various CIP and/or COP portions of the system are uniquely suited to the fermentation systems which rely heavily on internal recycling of fermentation components. Such internal recycling is well suited to the methods of the invention employing peracid compositions as these compositions that have sufficient longevity and compatibility with the fermentation source/materials.

In a preferred aspect, the peracid composition is introduced (e.g. injected) into a fermentation vessel (i.e. fermentor). In a further aspect, the peracid composition is introduced upstream from a fermentation tank, (e.g. in the mash cooler where bacterial infections often reside). Such introduction may further be in combination with traditional cleaning and sanitation practices that are routinely performed on the fermentation tank. The introduction of a peracid composition upstream from a fermentation tank may be combined with out CIP and/or CIP systems described herein.

In a further aspect, the peracid composition (or a portion thereof) remains in the vessel or fermentation system instead of being drained therefrom. The amount of peracid composition remaining in the vessel may vary according to the desired level of sanitization and dependent upon the stability of the peracid composition (including amount of peracid composition remaining in byproducts of the ethanol fermentation, e.g. distiller's grain). The residual or remaining peracid composition can be beneficially included with a mash source and act as a preservative for the fermentation process. The use of a residual amount of a peracid composition in a mash source of the fermentation process provides additional benefits as the mash source is a common infection point for the fermentation process.

Beneficially and unexpectedly, there methods of the invention do not require a rinse step to completely remove the peracid compositions. Many sanitizing methods employ a rinse step, such as rinsing an apparatus with other materials such as potable water.

It is to be understood that the methods may employ an aqueous or non-aqueous peracid composition. In addition, either a concentrate or use concentration of the peracid compositions can be applied to or brought into contact with an object by any conventional method or apparatus for applying an antimicrobial or cleaning compound to an object, such as disclosed for example in applications of use described in U.S. Pat. No. 7,507,429, which is herein incorporated by reference in its entirety. For example, the object can be wiped with, sprayed with, poured on, foamed on, and/or immersed in the compositions, or a use solution made from the compositions. The compositions can be sprayed, foamed, or wiped onto a surface; the compositions can be caused to flow over the surface, or the surface can be dipped into the compositions. These and other methods of contacting an object or a surface with the peracid composition are within the scope of the invention. Contacting can be manual or by machine.

The onsite production of the peracid composition is also included within the scope of the invention. Exemplary methods and/or apparatus for producing certain peracid compositions are disclosed for example in U.S. patent application Ser. Nos. 13/330,915, 13/330,981, 13/331,104, 13/331,304, 13/331,385 and 13/331,486 (Ecolab 2757USU1, 2757USU2, 2839USU1, 2943US01, 2969US01 and 2997US01), which are incorporated herein by reference in their entirety.

The methods may include the introduction of the peracid compositions at a temperature in the range of about 4° C. to 60° C. After introduction of the peracid composition, the peracid (e.g. solution) is held in the vessel and/or circulated throughout the system for a time sufficient for sanitization (e.g., to kill undesirable microorganisms). The contact time can vary based upon the concentration of the peracid compositions, method of applying the peracid compositions, temperature conditions, amount of soil, microorganisms or contamination on the surface or apparatus to be treated, or the like. In some aspects of the invention, the exposure time can be at least about 5 seconds, at least about 15 seconds, or more. In other embodiments, the exposure time is at least a few minutes. After the surfaces have been sanitized by means of the peracid compositions, the solution may be removed (e.g. drained from the system) or retained (in whole or in part) in the system for additional sanitizing benefit.

In some embodiments, the methods of the invention may further employ pressure and/or mechanical action with the application of the peracid composition. As one of skill in the art will appreciate, mechanical action may include for example, agitation, rubbing, brushing, etc. Agitation can be by physical scrubbing of the surface (e.g. vessel), through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., for example, about 20 to 60° C. to increase efficacy.

As one of skill in the art will ascertain as being within the scope of the invention, the amount of peracid composition provided to a fermentation system will vary based upon a number of factors. For example, the size, structural orientation, materials employed therein, contamination level of the system, and the like will affect the amount (and/or concentration) of peracid composition applied thereto. In some aspects, hundreds of gallons of peracid composition (e.g. solution) may be provided to a fermentation system. In other aspects, thousands of gallons of peracid composition (e.g. solution) may be provided to a fermentation system, including for CIP cleaning methods.

Further demonstration of the methods according to the invention is shown in FIG. 1 (referenced above).

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Initial laboratory testing to confirm the performance of peracid compositions to suppress *Lactobacillus* species and *Acetobacter* species in the fermentation process was conducted. The biocide fermentation tests were conducted using Vortexx ESF (peracetic acid+octanoic acid) and Whisper V (quaternary ammonium compound) each commercially-available from Ecolab, Inc. The methods of the testing included:

Obtaining fermentation flasks containing 100 ml of fermentation mixture (10% of yeast+*Lactobacillus brevis* infection (ATCC Deposit No. 14869)+brown sugar juice 19° Brix).

At Time zero (T=0)→10% of yeast+*Lactobacillus* infection (ATCC Deposit No. 14869)+brown sugar juice 19° Brix.

One hour after biocide addition in the flask (T=1)→10% of yeast+*Lactobacillus* infection (ATCC Deposit No. 14869)+brown sugar juice 19° Brix+Vortexx ESF or Whisper V.

Four hours after biocide addition in the flask (T=4)→10% of yeast+*Lactobacillus* infection (ATCC Deposit No. 14869)+brown sugar juice 19° Brix+Vortexx ESF or Whisper V.

Fermentation samples were plated in two types of agar medium before and after biocide addition aiming to count yeast and bacteria reduction after treatment. The objective of biocide treatment is to reduce bacterial contamination at least 100 times or "x" ($10^2$). Treatments were done in duplicate.

Figure 2:
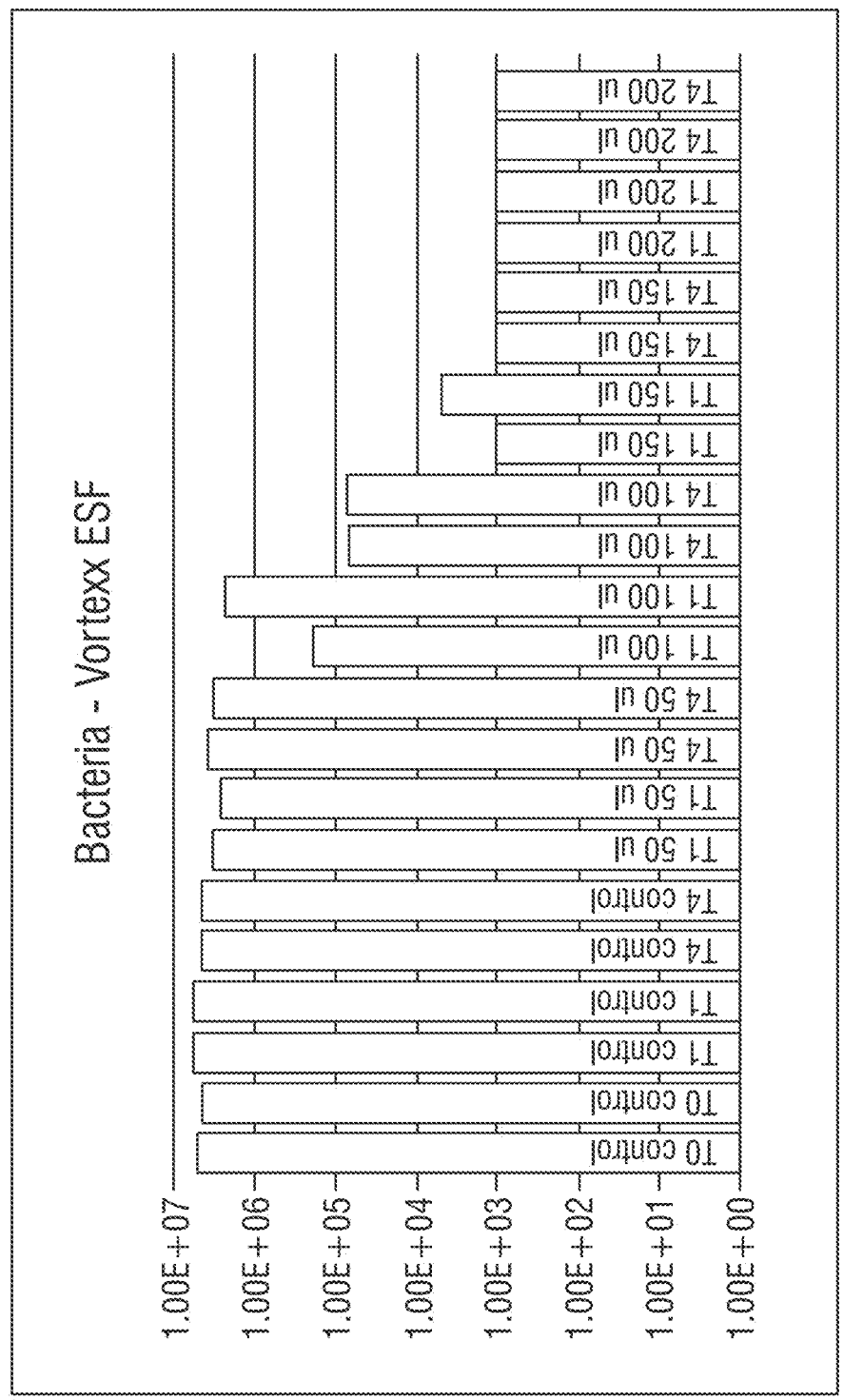
FIG. 2 shows a graph demonstrating the reduction in bacterial count in systems using the peracid compositions compared to control in fermentation processes according to the invention.

Fermentations where were added 150 and 200 ul of Vortexx ESF no bacterial growing were observed in a dilution of 10-3 after 1 and 4 hours of biocide addition. For this reason, the number of bacteria in these samples was lower than $1 \times 10^3$ cells/mL. The results using Vortexx ESF (peracetic acid+octanoic acid) are shown in FIG. 2 and Table 1 as described herein.

T0 Control—no biocide addition

T1 Control—no biocide addition. After 1 hour of fermentation.

T4 Control—no biocide addition. After 4 hours of fermentation.

T1—50 ul of biocide in 100 ml of fermentation (500 ppm of product)—after 1 hour of biocide addition.

T4—50 ul of biocide in 100 ml of fermentation (500 ppm of product)—after 4 hours of biocide addition.
T1—100 ul of biocide in 100 ml of fermentation (1000 ppm of product)—after 1 hour of biocide addition.
T4—100 ul of biocide in 100 ml of fermentation (1000 ppm of product)—after 4 hours of biocide addition.
T1—150 ul of biocide in 100 ml of fermentation (1500 ppm of product)—after 1 hour of biocide addition.
T4—150 ul of biocide in 100 ml of fermentation (1500 ppm of product)—after 4 hours of biocide addition.
T1—200 ul of biocide in 100 ml of fermentation (2000 ppm of product)—after 1 hour of biocide addition.
T4—200 ul of biocide in 100 ml of fermentation (2000 ppm of product)—after 4 hours of biocide addition.

Figure 4:
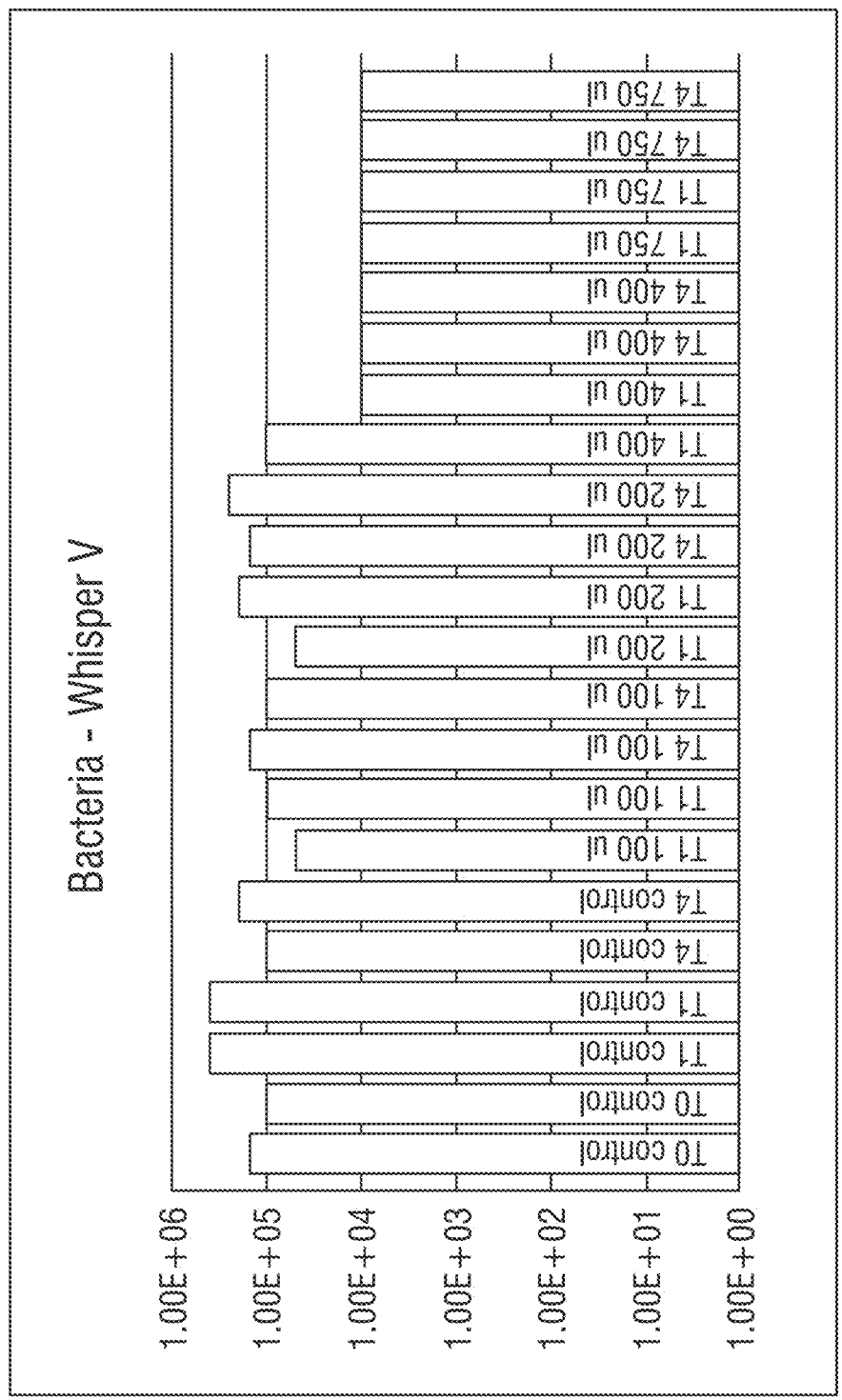
FIG. 4 shows a graph demonstrating the reduction in bacterial count in systems using a quaternary compound compositions compared to control in fermentation processes according to the invention.
Figure 5:
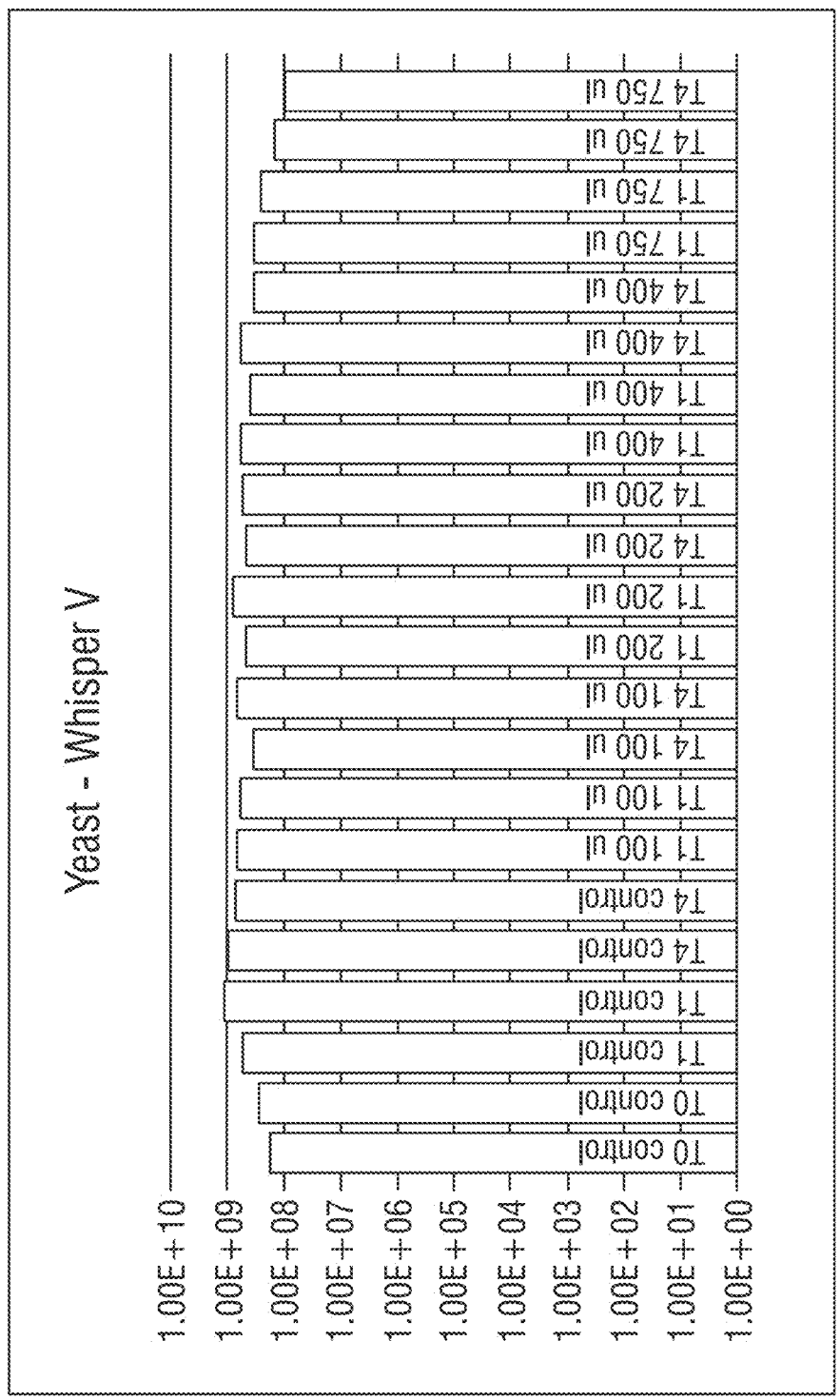
FIG. 5 shows a graph demonstrating no reduction in yeast in systems using a quaternary compound compared to control in fermentation processes according to the invention.

The results using Whisper V (quaternary ammonium compound) are shown in FIG. 4 and Table 3 as described herein. Fermentations where were added 400 and 750 ul of Whisper V no bacterial growing were observed in a dilution of 10-4. For this reason, the number of bacterial in these samples was lower than $1 \times 10^4$ cells/mL.

T0 Control—no biocide addition
T1 Control—no biocide addition. After 1 hour of fermentation.
T4 Control—no biocide addition. After 4 hours of fermentation.
T1—100 ul of biocide in 100 ml of fermentation (1000 ppm of product)—after 1 hour of biocide addition.

TABLE 1

VORTEXX ESF - BACTERIA

| | | | | | | | | | | | | | | |
|---|---|---|---|---|---|---|---|---|---|---|---|---|---|---|
| B0 | V | T0 | control | 5.00E+06 | B1 | V | T1 | 50 ul | 3.35E+06 | B1 | V | T4 | 50 ul | 3.90E+06 |
| B0 | V | T0 | control | 4.50E+06 | B2 | V | T1 | 50 ul | 2.65E+06 | B2 | V | T4 | 50 ul | 3.30E+06 |
| | | | | | B3 | V | T1 | 100 ul | 1.85E+05 | B3 | V | T4 | 100 ul | 7.00E+04 |
| | | | | | B4 | V | T1 | 100 ul | 2.25E+06 | B4 | V | T4 | 100 ul | 7.50E+04 |
| | | | | | B5 | V | T1 | 150 ul | 1.00E+03 | B5 | V | T4 | 150 ul | 1.00E+03 |
| | | | | | B6 | V | T1 | 150 ul | 5.00E+03 | B6 | V | T4 | 150 ul | 1.00E+03 |
| | | | | | B7 | V | T1 | 200 ul | 1.00E+03 | B7 | V | T4 | 200 ul | 1.00E+03 |
| | | | | | B8 | V | T1 | 200 ul | 1.00E+03 | B8 | V | T4 | 200 ul | 1.00E+03 |
| | | | | | B9 | V | T1 | control | 5.90E+06 | B9 | V | T4 | control | 4.50E+06 |
| | | | | | B10 | V | T1 | control | 5.95E+06 | B10 | V | T4 | control | 4.60E+06 |

Vortexx ESF demonstrates efficacy as a biocide to use during ethanol fermentation. It was observed a bacterial reduction in at least 10 times 1 hour after add 100 ul of Vortexx ESF in 100 ml of fermentation and at least 100 times 4 hours after biocide addition. We also observed that bacterial reduction after add 150 ul and 200 ul of Vortexx ESF in 100 ml of fermentation was 1000× lower comparing to control samples.

Figure 3:
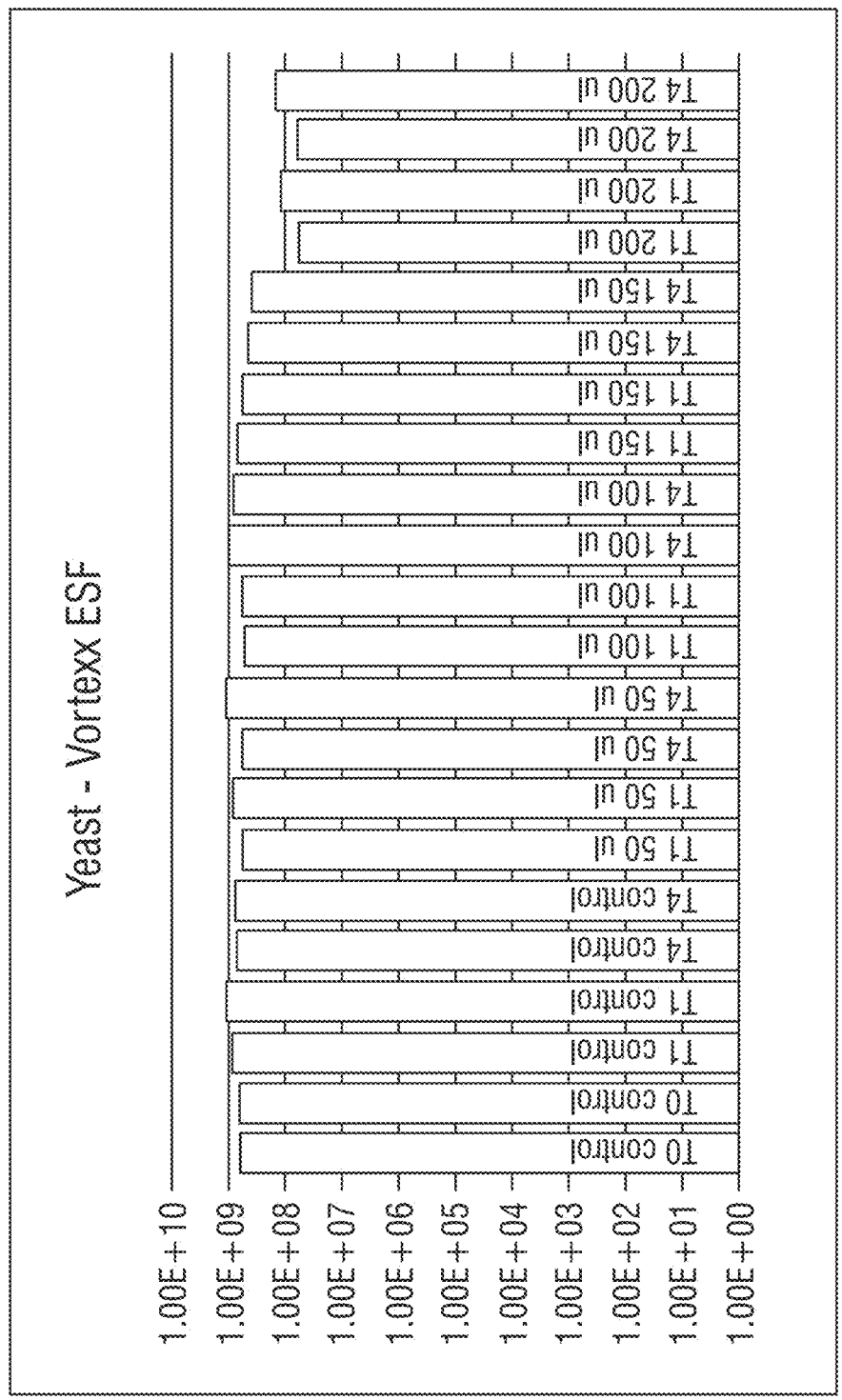
FIG. 3 shows a graph demonstrating no reduction in yeast in systems using the peracid compositions compared to control in fermentation processes according to the invention.

In addition, no significantly yeast reduction was observed after any dosage of Vortexx ESF, as shown in FIG. 3 in Table 2. Accordingly the methods of the invention show a clear benefit in the ethanol fermentation industry without causing any detrimental reduction in yeast cell numbers that would impair the efficiency of fermentation. However, according to preferred aspects of the invention, the biocide fermentation would preferably not be conducted using a peracid composition including peracetic acid, e.g. Vortexx ESF (peracetic acid+octanoic acid). This is due in part to the peracetic acid introducing an acetic acid which can result in false positive tests on quality control applications; the organic acid appears on plant quality control tests (e.g. Gas Chromatography) as a false indicator of infection with acid-forming bacteria.

T4—100 ul of biocide in 100 ml of fermentation (1000 ppm of product)—after 4 hours of biocide addition.
T1—200 ul of biocide in 100 ml of fermentation (2000 ppm of product)—after 1 hour of biocide addition.
T4—200 ul of biocide in 100 ml of fermentation (2000 ppm of product)—after 4 hours of biocide addition.
T1—400 ul of biocide in 100 ml of fermentation (4000 ppm of product)—after 1 hour of biocide addition.
T4—400 ul of biocide in 100 ml of fermentation (4000 ppm of product)—after 4 hours of biocide addition.
T1—750 ul of biocide in 100 ml of fermentation (7500 ppm of product)—after 1 hour of biocide addition.
T4—750 ul of biocide in 100 ml of fermentation (7500 ppm of product)—after 4 hours of biocide addition.

In an aspect of the invention a quaternary ammonium compound, e.g. Whisper V, is not a preferred compositions for use according to the invention. This is due to the preferred aspects of using compositions that lack any contamination residues in a subsequent animal feed product generated from the ethanol fermentation process.

TABLE 2

VORTEXX ESF - YEAST

| | | | | | | | | | | | | | | |
|---|---|---|---|---|---|---|---|---|---|---|---|---|---|---|
| L0 | V | T0 | control | 6.25E+08 | L1 | V | T1 | 50 ul | 6.00E+08 | L1 | V | T4 | 50 ul | 6.00E+08 |
| L0 | V | T0 | control | 6.50E+08 | L2 | V | T1 | 50 ul | 8.50E+08 | L2 | V | T4 | 50 ul | 1.10E+09 |
| | | | | | L3 | V | T1 | 100 ul | 5.50E+08 | L3 | V | T4 | 100 ul | 1.00E+09 |
| | | | | | L4 | V | T1 | 100 ul | 6.00E+08 | L4 | V | T4 | 100 ul | 8.50E+08 |
| | | | | | L5 | V | T1 | 150 ul | 7.00E+08 | L5 | V | T4 | 150 ul | 4.50E+08 |
| | | | | | L6 | V | T1 | 150 ul | 6.00E+08 | L6 | V | T4 | 150 ul | 4.00E+08 |
| | | | | | L7 | V | T1 | 200 ul | 5.90E+07 | L7 | V | T4 | 200 ul | 6.30E+07 |
| | | | | | L8 | V | T1 | 200 ul | 1.20E+08 | L8 | V | T4 | 200 ul | 1.50E+08 |
| | | | | | L9 | V | T1 | control | 9.00E+08 | L9 | V | T4 | control | 7.50E+08 |
| | | | | | L10 | V | T1 | control | 7.50E+08 | L10 | V | T4 | control | 8.00E+08 |

TABLE 3

WHISPER V - BACTERIA

| | | | | | | | | | | | | | | | |
|---|---|---|---|---|---|---|---|---|---|---|---|---|---|---|---|
| B0 | W | T0 | control | 1.50E+05 | B1 | W | T1 | 100 ul | 5.00E+04 | B1 | W | T4 | 100 ul | 1.50E+05 |
| B0 | W | T0 | control | 1.00E+05 | B2 | W | T1 | 100 ul | 1.00E+05 | B2 | W | T4 | 100 ul | 1.00E+05 |
| | | | | | B3 | W | T1 | 200 ul | 5.00E+04 | B3 | W | T4 | 200 ul | 1.50E+05 |
| | | | | | B4 | W | T1 | 200 ul | 2.00E+05 | B4 | W | T4 | 200 ul | 2.50E+05 |
| | | | | | B5 | W | T1 | 400 ul | 1.00E+05 | B5 | W | T4 | 400 ul | 10000 |
| | | | | | B6 | W | T1 | 400 ul | 1.00E+04 | B6 | W | T4 | 400 ul | 10000 |
| | | | | | B7 | W | T1 | 750 ul | 1.00E+04 | B7 | W | T4 | 750 ul | 10000 |
| | | | | | B8 | W | T1 | 750 ul | 1.00E+04 | B8 | W | T4 | 750 ul | 10000 |
| | | | | | B9 | W | T1 | control | 4.00E+05 | B9 | W | T4 | control | 1.00E+05 |
| | | | | | B10 | W | T1 | control | 4.00E+05 | B10 | W | T4 | control | 2.00E+05 |

It was not possible to affirm what is the best dosages of Whisper V into fermentation flasks to control bacterial infection because was not possible to count bacteria reduction after add 400 and 750 ul of this biocide into 100 ml of fermentation test. The minimum dilution plated (10-4), there was no bacterial growth (estimated bacterial cell number was lower than $10^4$ cells/ml). No significantly yeast reduction was observed after any dosage of Whisper V as shown in FIG. 5 and Table 4.

TABLE 4

| WHISPER V - YEAST | | | | | | | | | | | | | | |
|---|---|---|---|---|---|---|---|---|---|---|---|---|---|---|
| L0 | W | T0 | control | 1.80E+08 | L1 | W | T1 | 100 ul | 6.50E+08 | L1 | W | T4 | 100 ul | 3.50E+08 |
| L0 | W | T0 | control | 2.70E+08 | L2 | W | T1 | 100 ul | 6.00E+08 | L2 | W | T4 | 100 ul | 6.50E+08 |
| | | | | | L3 | W | T1 | 200 ul | 4.50E+08 | L3 | W | T4 | 200 ul | 4.50E+08 |
| | | | | | L4 | W | T1 | 200 ul | 8.00E+08 | L4 | W | T4 | 200 ul | 5.50E+08 |
| | | | | | L5 | W | T1 | 400 ul | 6.00E+08 | L5 | W | T4 | 400 ul | 6.00E+08 |
| | | | | | L6 | W | T1 | 400 ul | 4.00E+08 | L6 | W | T4 | 400 ul | 3.50E+08 |
| | | | | | L7 | W | T1 | 750 ul | 3.50E+08 | L7 | W | T4 | 750 ul | 1.50E+08 |
| | | | | | L8 | W | T1 | 750 ul | 2.50E+08 | L8 | W | T4 | 750 ul | 1.00E+08 |
| | | | | | L9 | W | T1 | control | 5.50E+08 | L9 | W | T4 | control | 9.50E+08 |
| | | | | | L10 | W | T1 | control | 1.10E+09 | L10 | W | T4 | control | 7.50E+08 |

Example 2

Additional testing was completed to analyze the efficacy of Vortexx ESF (peracetic acid+octanoic acid) (Ecolab, Inc.) and Octave (peroxyoctanoic acid) (Ecolab, Inc.) mixed peracid compositions for controlling bacterial contaminants in ethanol fermentation processes. As set forth in Example 1 there are inherent disadvantages to employing a peracid composition including peracetic acid/acetic acid and therefore there are superior peracid and mixed peracid compositions for use according to the methods of the invention that do not employ the peracetic acid.

The methods of the testing included:

Reagents

Solutions of Vortexx and Octave were provided by the Ecolab, Inc. The antibiotic Virginiamycin was purchased from SantaCruz Biotechnology. Ethanol Red yeast (Fermentis), and *Lactobacillus fermentum* were revived from 10% glycerol stocks maintained at 70 C. Yeast was grown at 30 C under aerobic conditions in either liquid YPD medium or on YPD agar prior to use in propagations and fermentations. Bacteria were grown at 30 C under anaerobic conditions in either liquid MRS broth, and or on MRS agar plates. Liquefied corn mash and gluco-amylase enzyme was provided by Illinois River Energy (Rochelle, Ill.).

Fermentations

Fermentations were conducted in Wheaton glass bottles placed in a 30 C recirculating water bath atop an 8-position magnetic stir-plate. Each bottle was sealed with a rubber septum cap and connected through ⅛" tubing to a respirometer instrument (Challenger Instruments), which quantified the off-gassing of $CO_2$ during fermentation.

Corn mash fermentations were conducted in 0.5 L Wheaton bottles, each containing the following typical components: liquefied corn mash (400 grams), gluco-amylase (0.33 mL), 50% urea solution (0.67 grams), and propagated yeast (20 mL). When antibiotics or mixed peracid products were used they were added with 800 microliters of water at the bottom of the bottle before filling with corn mash. The water was intended to simulate the CIP rinse water volume. Virginiamycin was used at 0.5 ppm or 1 ppm, and Vortexx or Octave was used between 2.1 and 30 percent in the rinse water volume.

MRS broth fermentations were conducted in 0.125 L Wheaton bottles, each containing the 100 mL of MRS broth and 4 mL propagated bacteria. When antibiotics or mixed peracid products were used they were added with 200 microliters of water at the bottom of the bottle before filling with MRS broth.

Measurement of Residual Sugars, Acids, and Alcohols

In preparation for HPLC analysis, completed fermentation samples were centrifuged for 10 minutes at 1000 rpm and the supernatant filtered through 0.45 micron nylon syringe filters. Filtered samples were diluted 1:50 in 2 mM $H_2SO_4$ mobile phase prior to injection into the column (Aminex HPX-87H (300×7.8 mm) with guard column). The column flow rate was 0.4 mL/min, the temperature was 25 degrees Celsius, and the run time was 50 minutes per sample. Analytes were detected using a refractive index detector (recorder range—512 uRIU/FS; integrator range—125 uRIU/V; temperature—30° C.; response time—0.5 seconds; polarity—positive; baseline shift—40 mV; sequence—standard).

Calibration of the HPLC instrument was performed using a fuel ethanol residual saccharide mix purchased from Sigma Aldrich (#48468-U). A stock solution was made by diluting the standard ten-fold in mobile phase. Refractive Index detectors tend to be fairly sensitive, thus it is recommended diluting the standards and samples in the same mobile phase running through the column on the HPLC system. All subsequent standards are created by making further dilutions of the stock standard solution after it has stirred for a sufficient amount of time (at least 15 minutes). The eight compounds monitored by HPLC along with their respective retention times are shown in Table 5. Standard K is the stock standard dilution, and all letters from B to J are further dilutions of this standard. The dilution factors were multiplied by the actual concentration listed on the COA, which allowed the concentration columns for each compound to be determined. Since resolution between dextrin, maltotriose and maltose is relatively poor, the height of these compounds provided a more accurate determination of their concentrations. For all other compounds, area is used to develop a calibration curve.

TABLE

| Standards | | Standard dilutions (6400-pg107) |
|---|---|---|
| Dextrin - 9.9 min | B | 0.000220162 |
| Maltotriose - 10.7 min | C | 0.000717274 |
| Maltose - 11.5 min | D | 0.002148433 |
| D-Glucose - 13.6 min | E | 0.004302416 |
| L-(+)-Lactic Acid - 19.1 min | F | 0.007912708 |
| Glycerol - 20.1 min | G | 0.012416336 |
| Acetic Acid - 23.5 min | H | 0.017314458 |
| Ethanol - 31.8 min | I | 0.024019447 |
| | J | 0.048444897 |
| | K | 0.114749254 |

| Conc (ppm) | Height | Rf |
|---|---|---|
| Dextrin - 9.9 min $y = 0.3976x - 4.1809$ | | |
| 7.2 | 1.191 | 6.007788679 |
| 23.3 | 5.830 | 3.998522966 |
| 69.8 | 23.819 | 2.931444198 |
| 139.8 | 50.639 | 2.761281395 |
| 257.2 | 95.872 | 2.682357805 |
| 403.5 | 156.405 | 2.580038531 |
| 562.7 | 219.514 | 2.563480689 |
| 780.6 | 305.321 | 2.556758388 |
| 1574.5 | 621.484 | 2.533386457 |
| 3729.4 | 1478.932 | 2.52165127 |
| Average - | | 3.179451012 |
| Maltotriose - 10.7 min $y = 0.5607x - 0.0825$ | | |
| 2.2 | 1.29 | 1.69619241 |
| 7.1 | 4.01 | 1.770824861 |
| 21.3 | 12.00 | 1.772161785 |
| 42.6 | 23.90 | 1.782023304 |
| 78.3 | 43.85 | 1.786286506 |
| 122.9 | 69.08 | 1.779411238 |
| 171.4 | 95.81 | 1.789113118 |
| 237.8 | 133.13 | 1.786127597 |
| 479.6 | 268.01 | 1.789535566 |
| 1136.0 | 637 | 1.782763044 |
| Average - | | 1.772408487 |
| Maltose - 11.5 min $y = 0.5128x + 0.0199$ | | |
| 4.4 | 2.30 | 1.896135056 |
| 14.2 | 7.28 | 1.950826289 |
| 42.5 | 21.97 | 1.936406204 |
| 85.2 | 43.83 | 1.943818415 |
| 156.7 | 80.36 | 1.949718961 |
| 245.8 | 126.49 | 1.943580178 |
| 342.8 | 175.51 | 1.953281395 |
| 475.6 | 243.96 | 1.94943864 |
| 959.2 | 491.06 | 1.953339725 |
| 2272.0 | 1165 | 1.949694232 |
| Average - | | 1.941838318 |

TABLE-continued

| Conc (ppm) | Area | Rf |
|---|---|---|
| D-Glucose - 13.6 min $y = 15703x + 13136$ | | |
| 4.4 | 87063 | 5.03225E-05 |
| 14.3 | 234463 | 6.08784E-05 |
| 42.8 | 687080 | 6.22254E-05 |
| 85.6 | 1360558 | 6.29287E-05 |
| 157.5 | 2482933 | 6.34181E-05 |
| 247.1 | 3915826 | 6.30991E-05 |
| 344.6 | 5425713 | 6.35046E-05 |
| 478.0 | 7520488 | 6.3558E-05 |
| 964.1 | 15101833 | 6.38369E-05 |
| 2283.5 | 35888120 | 6.36286E-05 |
| Average - | | 6.15302E-05 |
| L-(+)-Lactic Acid - 19.1 min $y = 10233x - 2285.2$ | | |
| 0.7 | 6583 | 0.000100332 |
| 2.2 | 22005 | 9.77878E-05 |
| 6.4 | 62333 | 0.000103401 |
| 12.9 | 128172 | 0.000100703 |
| 23.7 | 240902 | 9.85385E-05 |
| 37.2 | 379506 | 9.81513E-05 |
| 51.9 | 534629 | 9.71578E-05 |
| 72.1 | 732351 | 9.83932E-05 |
| 145.3 | 1476872 | 9.84071E-05 |
| 344.2 | 3523625 | 9.7697E-05 |
| Average - | | 9.92079E-05 |
| Glycerol - 20.1 min $y = 12718x + 25535$ | | |
| 2.2 | 34346 | 6.34603E-05 |
| 7.1 | 104536 | 6.79288E-05 |
| 78.3 | 1105441 | 7.08639E-05 |
| 122.9 | 1593811 | 7.71244E-05 |
| 171.4 | 2185621 | 7.84277E-05 |
| 237.8 | 3026638 | 7.85666E-05 |
| 479.6 | 6095898 | 7.86766E-05 |
| 1136.0 | 14487479 | 7.84138E-05 |
| Average - | | 6.80889E-05 |
| Acetic Acid - 23.5 min $y = 6606.4x + 1837.9$ | | |
| 0.7 | 5127 | 0.000133119 |
| 2.2 | 15150 | 0.000146769 |
| 6.7 | 44331 | 0.000150237 |
| 13.3 | 92391 | 0.000144359 |
| 24.5 | 166629 | 0.00014721 |
| 38.5 | 257424 | 0.000149522 |
| 53.7 | 356104 | 0.000150728 |
| 74.5 | 495375 | 0.000150311 |
| 150.2 | 988787 | 0.000151882 |
| 355.7 | 2353399 | 0.000151153 |
| Average - | | 0.000147126 |
| Ethanol - 31.8 min $y = 6158.6x - 42237$ | | |
| 26.2 | 155449 | 0.000168398 |
| 85.3 | 490636 | 0.000173823 |
| 255.4 | 1512846 | 0.000168853 |
| 511.6 | 3048365 | 0.000167814 |
| 940.8 | 5741237 | 0.000163871 |
| 1476.3 | 9071669 | 0.000162738 |
| 2058.7 | 12649396 | 0.00016275 |
| 2855.9 | 17570209 | 0.000162543 |
| 5760.1 | 35417028 | 0.000162636 |
| Average - | | 0.000165936 |

The objectives of the analysis included measuring residual levels of peracid and hydrogen peroxide after exposure to fermentable substrate and to yeast; inoculating contaminating bacterial species with the fermentable substrate and determining the reduction in viable cells after exposure to the mixed peracid products; and investigation of any negative impact of peracids on normal fermentation performance and yeast activity.

Results

The concentrations of peracid and hydrogen peroxide actives at various stages of filling the fermentation tank were analyzed. This analysis used the initial active concentrations reported in the catalog sheets for Vortex and Octave. It was also assumed that 5.0% Vortexx or 2.1% Octave were added to the CIP rinse water. The rinse water volume was assumed to be 0.2% of the fermenter tank volume. The methods simulated the dilution of the sanitizing solution of the peracid and hydrogen peroxide actives (peracid composition) in the tank due to filling with mash. As a result, the concentrations were constantly diluted in the mash as the tank fills. This is shown below in Table 6, illustrating the combined effect of dilution and reaction of the actives with sugars in the mash. The table demonstrates the dynamic occurring with mash addition.

Prior research (Urea Hydrogen Peroxide Reduces the Number of Lactobacilli, Nourishes Yeast, and Leaves No Residue in the Ethanol Fermentation. N. V. Narendarath, K. C. Thomas, M. W. Ingledew (2000). Appl. Env. Microbiology, Vol. 66, pp. 4187-4192) found that 600 ppm of hydrogen peroxide and 2 hours of contact time in the absence of yeast was required for effective bacterial control.

As can be seen in Table 6 (dilution corrected active concentrations), the peracid and hydrogen peroxide concentrations are well below 100 ppm even when the fermenter is only 10% full, demonstrating that the dilution of the CIP rinse volume with fermentable substrate is a challenge associated with the invention. However, the actual concentrations are likely to be much less than those reported in Table 6. Further reductions in the active concentrations will certainly occur as the peracids attack the highly loaded organic matter in the fermentable substrate, and as the yeast degrade the hydrogen peroxide.

the decay rate shown here could be expected to increase by 10-fold when using full strength corn mash. Numerous additional factors affect decay rate, including for example, diffusion rate of the sanitizing solution in the viscous mash being added. *Peracid Chemistries for Controlling Lactobacilli in MRS Broth*

Figure 6:
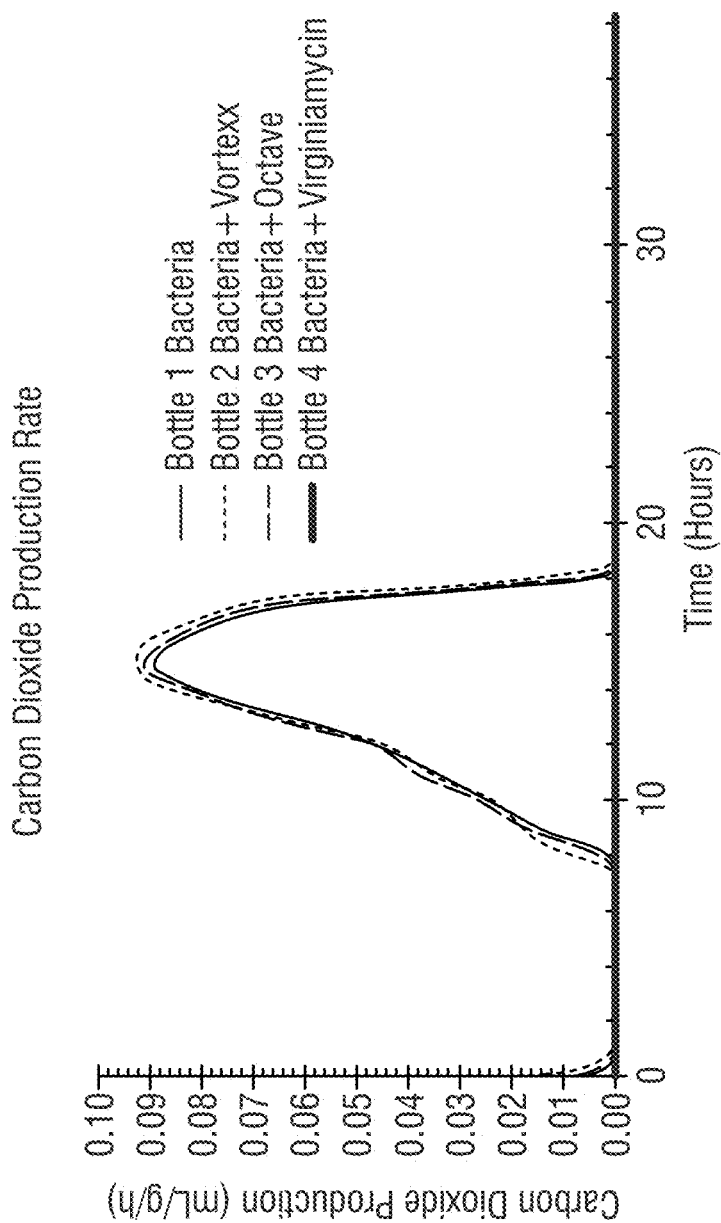
FIG. 6 shows a graph demonstrating carbon dioxide production in systems treated with peracid chemistries in the rinse water alone to control bacterial growth, and photographs of the tested bottles of fermentation liquids.

MRS broth, which contains only 0.6% solids compared to typical liquefied corn mash at 30% solids, represents a relatively simple test of the effectiveness of the peracid chemistries for controlling *Lactobacillus* growth. A pure culture of *L. fermentum* was inoculated into MRS broth at a starting concentration of $1 \times 10^5$ cell/mL. The MRS broth with bacteria was split into four different bottles. The first bottle contained no antibiotic or peracid. The second and third bottles contained 5% Vortexx or 5% Octave, respectively, in the rinse water. The fourth bottle contained 1 ppm virginiamycin. All bottles were placed monitored via respirometry under identical conditions. As seen in FIG. 6, bottles 1, 2, and 3 produced identical amounts of $CO_2$ with exactly the same kinetics. Bottle 4 failed to produce any $CO_2$ and exhibited no bacterial growth. These observations indicate that applying peracid chemistries in the rinse water will not control bacterial growth alone, and therefore would need to be combined with out cleaning steps (e.g. CIP/COP, etc.).

Impact of Peracid Chemistries on Yeast in Corn Mash

Several corn mash fermentation experiments were performed to assess the potential impact of the peracid chem-

TABLE 6

|  |  | Vortexx | | | Octave | | |
| --- | --- | --- | --- | --- | --- | --- | --- |
| tank level | tank volume | Conc. | [PAA] ppm | [H202] ppm | Conc. | [POA] ppm | [H202] ppm |
| 0.00% | 1000 | 5.00% | 2200.0 | 3450.0 | 2.10% | 197.4 | 1596.0 |
| 10.00% | 51000 | 0.10% | 43.1 | 67.6 | 0.04% | 3.9 | 31.3 |
| 20.00% | 101000 | 0.050% | 21.8 | 34.2 | 0.021% | 2.0 | 15.8 |
| 30.00% | 151000 | 0.033% | 14.6 | 22.8 | 0.014% | 1.3 | 10.6 |
| 40.00% | 201000 | 0.025% | 10.9 | 17.2 | 0.010% | 1.0 | 7.9 |
| 50.00% | 251000 | 0.020% | 8.8 | 13.7 | 0.008% | 0.8 | 6.4 |

Survival of Vortexx in Corn Mash

Corn mash from a local dry-grind ethanol plant was diluted 1:10 with water. Vortexx was mixed into the 10-fold diluted corn mash at 1:1000 ratio. PAA test strips from LaMotte were used to track the survival of Vortexx in the corn mash. After 60 minutes, the Vortexx was almost completely consumed by the corn mash.

As a control, pure water was treated with the same Vortexx solution at 1:1000 ratio. No detectable consumption of Vortexx was observed over the same 60 minute period.

This experiment demonstrates that corn mash, even at 10% of its normal solids concentration, possesses an apparent demand for the oxidizing chemistries in Vortexx. Thus, istries on yeast activity. Three sets of fermentation experiments were performed, and in each set eight different fermentations were conducted to allow for variation of the bacterial innocula and anti-bacterial control strategies.

Figure 7A:
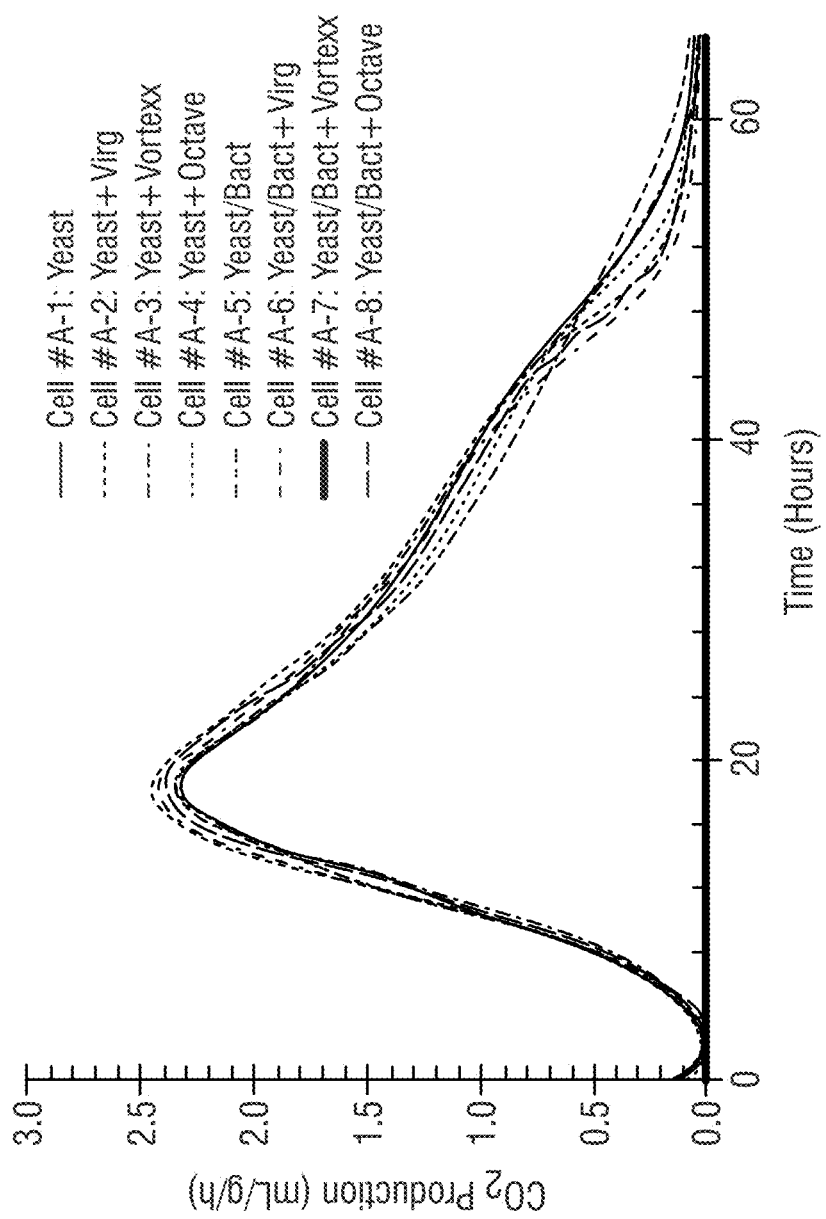
FIGS. 7A-B and FIGS. 8A-8B show graphs demonstrating the effect of peracid compositions in the rinse water and impact on total volume of $CO_2$ produced or the rate of $CO_2$ production.
Figure 7B:
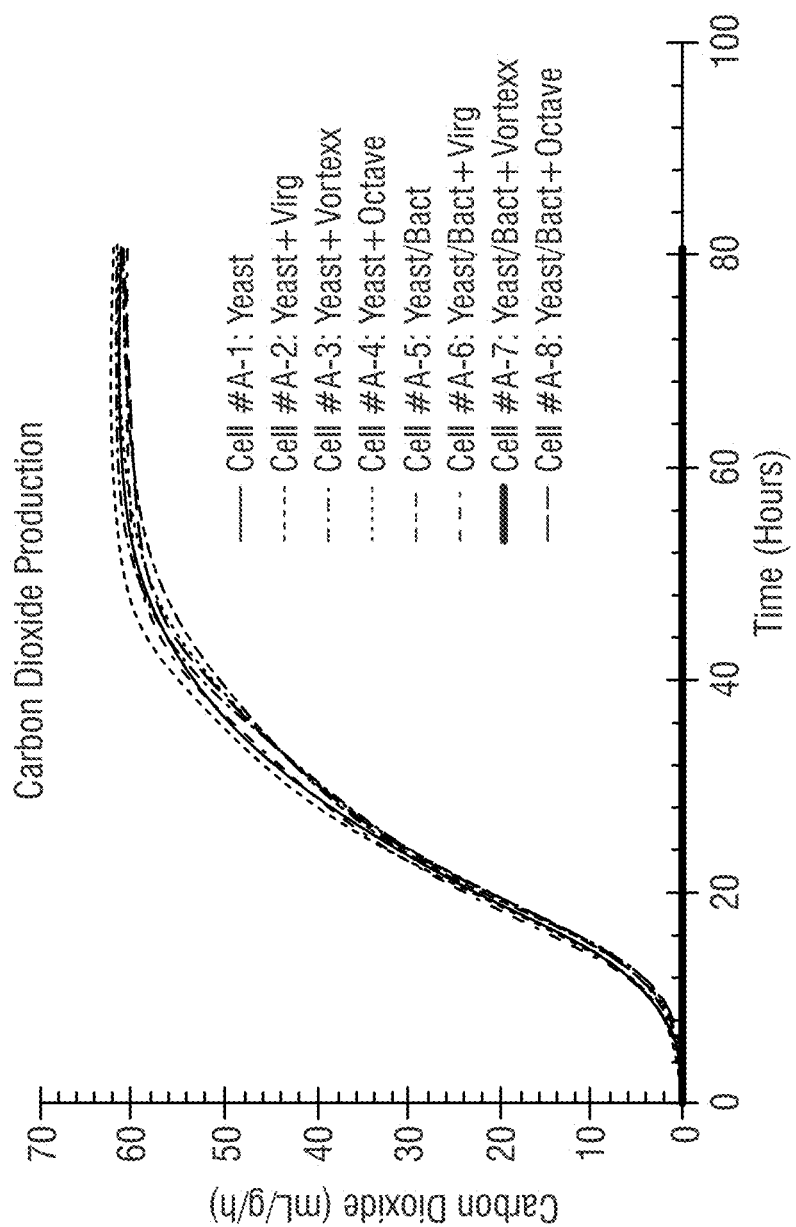

In the first experiment, 5% Vortexx or 5% Octave in the rinse water had absolutely no impact on the total volume of $CO_2$ produced or the rate of $CO_2$ production (FIG. 7).

HPLC analysis of the completed fermentation samples also revealed no differences among the eight samples in residual sugars, acids, and alcohol at the end of fermentation (Table 7).

TABLE 7

| Sample | Dextrin Conc (%) | Maltitriose Conc (%) | Maltose Conc (%) | Glucose Conc (%) | Lact Acd Conc (%) | Glycerol Conc (%) | Acetic Acid Conc (%) | Ethanol Conc (%) |
| --- | --- | --- | --- | --- | --- | --- | --- | --- |
| 1 | 1.03 | ND < 0.20 | 0.37 | 0.44 | 0.6 | 1.98 | 0.1 | 14.55 |
| 2 | 1.03 | ND < 0.20 | 0.36 | 0.43 | 0.56 | 1.99 | 0.1 | 14.71 |
| 3 | 1.05 | ND < 0.20 | 0.38 | 0.41 | 0.61 | 1.99 | 0.1 | 14.69 |
| 4 | 1.04 | ND < 0.20 | 0.38 | 0.39 | 0.61 | 1.99 | 0.09 | 14.66 |
| 5 | 1.03 | ND < 0.20 | 0.39 | 0.42 | 0.65 | 1.99 | 0.09 | 14.6 |
| 6 | 1.04 | ND < 0.20 | 0.37 | 0.42 | 0.59 | 1.99 | 0.1 | 14.62 |
| 7 | 1.03 | ND < 0.20 | 0.38 | 0.42 | 0.62 | 1.98 | 0.09 | 14.55 |
| 8 | 1.03 | ND < 0.20 | 0.38 | 0.4 | 0.62 | 1.98 | 0.09 | 14.61 |

Figure 8A:
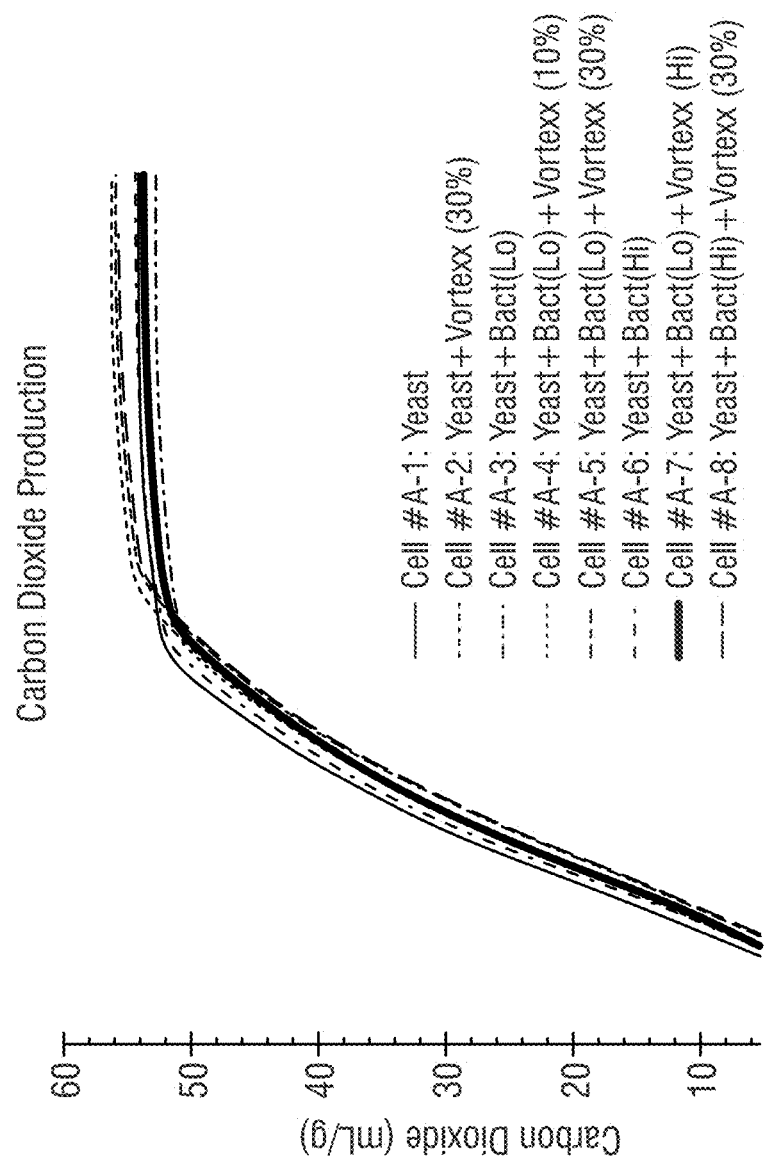
Figure 8B:
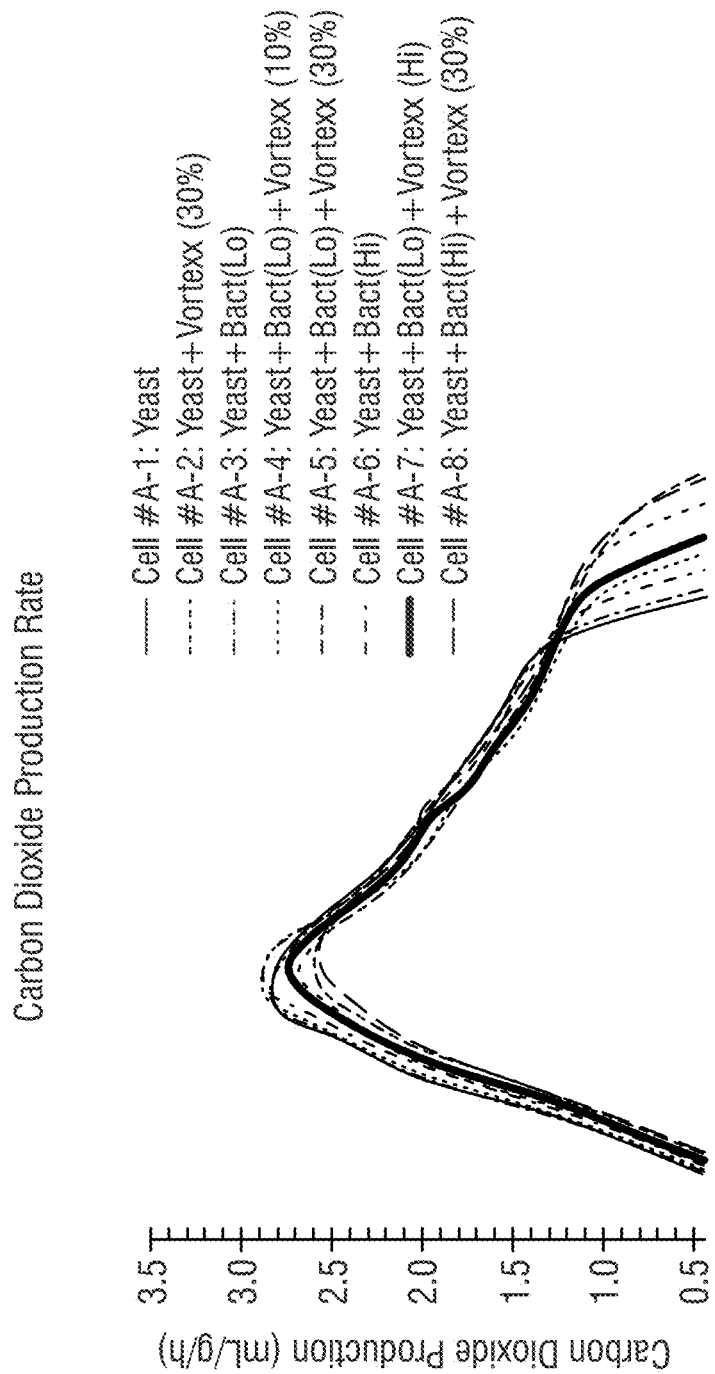

In the second experiment, 10% Vortexx or 30% Vortexx in the rinse water were shown to slow down the initial rate of $CO_2$ production, but ultimately there was no impact on the total volume of $CO_2$ produced (FIG. 8).

HPLC analysis of the completed fermentation samples also revealed no differences among the eight samples in residual sugars, acids, and alcohol at the end of fermentation (Table 8).

TABLE 8

| Sample | Dextrin Conc (%) | Maltitriose Conc (%) | Maltose Conc (%) | Glucose Conc (%) | Lact Acd Conc (%) | Glycerol Conc (%) | Acetic Acid Conc (%) | Ethanol Conc (%) |
|---|---|---|---|---|---|---|---|---|
| 1 | 0.92 | ND < 0.20 | 0.36 | 0.18 | 0.63 | 1.78 | 0.08 | 13.84 |
| 2 | 0.92 | ND < 0.20 | 0.37 | 0.19 | 0.6  | 1.72 | 0.11 | 13.96 |
| 3 | 0.93 | ND < 0.20 | 0.36 | 0.16 | 0.62 | 1.84 | 0.1  | 13.93 |
| 4 | 0.93 | ND < 0.20 | 0.37 | 0.17 | 0.67 | 1.79 | 0.08 | 14.02 |
| 5 | 0.93 | ND < 0.20 | 0.38 | 0.19 | 0.63 | 1.72 | 0.09 | 14.02 |
| 6 | 0.94 | ND < 0.20 | 0.39 | 0.2  | 0.64 | 1.82 | 0.09 | 13.93 |
| 7 | 0.92 | ND < 0.20 | 0.41 | 0.2  | 0.71 | 1.83 | 0.11 | 13.88 |
| 8 | 0.93 | ND < 0.20 | 0.41 | 0.19 | 0.67 | 1.74 | 0.09 | 13.92 |

The inventions being thus described, it will be obvious that the same may be varied in many ways. Such variations are not to be regarded as a departure from the spirit and scope of the inventions and all such modifications are intended to be included within the scope of the following claims. Since many embodiments can be made without departing from the spirit and scope of the invention, the invention resides in the claims.

What is claimed is:

1. A method for reducing and/or eliminating microbial populations of yield loss organisms in a biofuel fermentation system comprising:
   applying a peracid composition to sanitize a fermentation system, wherein the peracid composition comprises a short chain peracid and a sequestrant wherein the fermentation system comprises one or more fermentation vessels, pipes and/or components;
   providing or obtaining a mash source in said fermentation system; and
   reducing and/or eliminating a microbial population of yield loss organisms in said fermentation system.

2. The method of claim 1, wherein the yield loss organisms are lactic acid bacteria and/or acetic acid bacteria.

3. The method of claim 1, wherein the peracid composition comprises peroxyformic acid, formic acid, hydrogen peroxide, a sequestrant, and water and does not include acetic acid and/or peracetic acid.

4. The method of claim 1, wherein the peracid composition comprises from about 0.5 wt-% to about 5 wt-% peroxyformic acid, from about 1 wt-% to about 10 wt-% formic acid, from about 5 wt-% to about 97 wt-% water, from about 0 wt-% to about 20 wt-% anionic surfactant, from about 0 wt-% to about 10 wt-% oxidizing agent; about 0 wt-% to about 35 wt-% inorganic acid, and from about 0 wt-% to about 5 wt-% sequestrant.

5. The method of claim 1, further comprising fermenting a fermentable mash in the presence of at least a portion of said peracid composition, and yeast in a vessel to produce ethanol and a solids content, wherein said peracid composition controls growth of bacteria in the mash without reducing yeast population; and distilling the fermented mash to separate at least a portion of the ethanol from said solids content.

6. A method for reducing yield loss in ethanol fermentation processes comprising:
   applying a peracid composition to sanitize a fermentation system, wherein the peracid composition comprises a short chain peracid and a sequestrant;
   fermenting a mash in the presence of at least a residual portion of said peracid composition and yeast in a vessel of said fermentation system to produce ethanol and a solids content;
   reducing a microbial population of lactic acid bacteria and/or acetic acid bacteria; and
   distilling the fermented mash to separate at least a portion of the ethanol from said solids content,
   wherein the antimicrobial efficacy of said peracid composition does not interfere with yeast fermentation.

7. The method of claim 6, wherein said peracid composition is applied to said fermentation system for providing sanitizing of said system without requiring a rinse step of said fermentation system, and wherein said portion of said peracid composition is a residual amount remaining in said vessel after sanitizing.

8. The method of claim 6, wherein the peracid composition comprises peroxyformic acid, formic acid, hydrogen peroxide, a sequestrant, and water.

9. The method of claim 6, wherein the lactic acid bacteria and/or acetic acid bacteria are *Lactobacillus* species, *Acetobacter* species or combinations thereof.

10. A method for replacing antibiotics in biofuel fermentation processes comprising:
    replacing an antibiotic used in a fermentation process to reduce and/or eliminate *Lactobacillus* and/or *Acetobacter* species with a peracid composition for application to a fermentation system; and
    introducing the peracid composition to a mash source, wherein the peracid composition comprises from about 0.0005 wt-% to about 5 wt-% peroxyformic acid, from about 1 wt-% to about 10 wt-% formic acid, from about 5 wt-% to about 97 wt-% water, from about 0 wt-% to about 20 wt-% anionic surfactant, from about 0 wt-% to about 10 wt-% oxidizing agent; about 0 wt-% to about 35 wt-% inorganic acid, and from about 0 wt-% to about 5 wt-% sequestrant, and wherein the peracid composition does not interfere with yeast fermentation in a fermentation process;
    wherein the peracid composition does not introduce to the fermentation system a source of acetic acid and/or peracetic acid.

11. The method of claim 10, wherein the peracid composition comprises from about 0.5 wt-% to about 5 wt-% peroxyformic acid, from about 1 wt-% to about 10 wt-% formic acid, from about 5 wt-% to about 97 wt-% water, from about 1 wt-% to about 20 wt-% anionic surfactant, from about 5 wt-% to about 10 wt-% oxidizing agent; about 15 wt-% to about 35 wt-% inorganic acid, and from about 1 wt-% to about 5 wt-% sequestrant.

12. The method of claim 10, further comprising fermenting the mash source in the presence of at least a portion of said peracid composition, and yeast in a vessel to produce ethanol and a solids content, wherein said peracid composition controls growth of bacteria in the mash without reducing yeast population; and distilling the fermented mash to separate at least a portion of the ethanol from said solids content.

13. The method of claim 12, further comprising obtaining a distillers dried grains product from said solid contents containing less than about 1000 ppm of the peracid composition.

14. The method of claim 10, wherein the peracid composition is introduced to the fermentation process within a clean-in-place application to clean the fermentation systems employed for the fermentation process.

15. The method of claim 14, wherein the peracid composition is introduced either upstream from a fermentation vessel or directly into the fermentation vessel.

16. The method of claim 14, wherein the peracid composition or a portion of the peracid composition is retained in the fermentation vessel after the clean-in-place application and used for reducing and/or eliminating the *Lactobacillus* and/or *Acetobacter* species during the fermentation process.

17. The method of claim 10, wherein the peracid composition is introduced to the fermentation process as a direct additive to the mash source.

18. The method of claim 10, wherein the peracid compositions have low or no adverse environmental impact.

19. The method of claim 1, wherein the peracid composition comprises peroxyformic acid and a medium chain peracid.

* * * * *